(12) United States Patent
St Amant

(10) Patent No.: US 10,373,466 B1
(45) Date of Patent: Aug. 6, 2019

(54) SYSTEMS, DEVICES, AND/OR PROCESSES FOR TRACKING BEHAVIORAL AND/OR BIOLOGICAL STATE

(71) Applicant: ARM Ltd., Cambridge (GB)

(72) Inventor: Renee Marie St Amant, Austin, TX (US)

(73) Assignee: ARM Ltd., Cambridge (GB)

( * ) Notice: Subject to any disclaimer, the term of this patent is extended or adjusted under 35 U.S.C. 154(b) by 0 days.

(21) Appl. No.: 15/922,644

(22) Filed: Mar. 15, 2018

(51) Int. Cl.
G08B 21/04 (2006.01)
A61B 5/16 (2006.01)
G06N 20/00 (2019.01)

(52) U.S. Cl.
CPC .......... *G08B 21/0423* (2013.01); *A61B 5/163* (2017.08); *G06N 20/00* (2019.01)

(58) Field of Classification Search
CPC ............ G08B 21/0423; G08B 21/0476; G08B 21/0453; G08B 21/002; G08B 21/0211; A61B 5/163; G06N 99/005; G06N 20/00
USPC .......................................... 340/539.11, 573.1
See application file for complete search history.

(56) References Cited

U.S. PATENT DOCUMENTS

| 9,704,209 B2 * | 7/2017 | Proud .................... G06Q 50/24 |
| 9,997,082 B2 * | 6/2018 | Kaleal .................... G06T 19/00 |
| 2004/0133453 A1 | 7/2004 | Jomini et al. |
| 2009/0312998 A1 * | 12/2009 | Berckmans ............ A61B 5/024 703/11 |
| 2010/0003653 A1 * | 1/2010 | Brown ..................... G09B 5/00 434/236 |
| 2011/0256520 A1 * | 10/2011 | Siefert ..................... G09B 5/10 434/322 |
| 2014/0218187 A1 | 8/2014 | Chun et al. |
| 2014/0306821 A1 * | 10/2014 | Rahman .................. G05B 1/01 340/539.11 |
| 2016/0270717 A1 * | 9/2016 | Luna ...................... G16H 50/20 |
| 2017/0018008 A1 | 1/2017 | Hajiyev et al. |
| 2017/0202509 A1 * | 7/2017 | Sanderson ........... A61B 5/4836 |
| 2017/0368936 A1 | 12/2017 | Kojima |
| 2018/0218123 A1 * | 8/2018 | Gomez Sanchez .... G16H 50/20 |

FOREIGN PATENT DOCUMENTS

CN 203438860 U 2/2014

OTHER PUBLICATIONS

ETHzürich Wearable devices, Screenshots of youtube video, www.youtube.com/watch?v=Qi34rm0gSZA, retrieved Nov. 28, 2018, 15 pages.
U.S. Appl. No. 15/922,671, filed Mar. 15, 2018, 121 pgs.
U.S. Appl. No. 15/922,687, filed Mar. 15, 2018, 146 pgs.
Invitation to Pay Additional Fees and, Where Applicable, Protest Fee, App. No. PCT/682019/050691, dated Jun. 18, 2019, 4 Pages.
Communication Relating to the Results of the Partial International Search, App. No. PCT/GB2019/050691, dated Jun. 18, 2019, 11 Pages.

* cited by examiner

*Primary Examiner* — Hung T Nguyen
(74) *Attorney, Agent, or Firm* — Berkeley Law & Technology Group, LLP

(57) ABSTRACT

Subject matter disclosed herein may relate to systems, devices, and/or processes for tracking signals and/or states representative of behavioral and/or biological state.

20 Claims, 7 Drawing Sheets

SYSTEMS, DEVICES, AND/OR PROCESSES FOR TRACKING BEHAVIORAL AND/OR BIOLOGICAL STATE

RELATED APPLICATIONS

This patent application is related to U.S. Ser. No. 15/922,671 entitled Systems, Devices, and/or Processes for Behavioral Content Processing and U.S. Ser. No. 15/922,687 entitled Systems, Devices, and/or Processes for Behavioral and/or Biological State Processing, all filed herewith, and all hereby incorporated by reference in their entirety.

BACKGROUND

Field

Subject matter disclosed herein may relate to systems, devices, and/or processes for tracking signals and/or states representative of behavioral and/or biological state.

Information

Integrated circuit devices, such as processors, for example, may be found in a wide range of electronic device types. For example, one or more processors may be used in mobile devices, such as cellular phones, for example, as well as in computers, digital cameras, tablet devices, personal digital assistants, wearable devices, etc. Mobile devices and/or other computing devices, for example, may include integrated circuit devices, such as processors, to process signals and/or states representative of a diverse of content types for a variety of purposes. With an abundance of diverse content being accessible, signal and/or state processing techniques continue to evolve. At times, however, processing signals and/or states representative of diverse content may prove to be relatively resource-demanding, which may present a number of challenges including, for example, increased processing time, storage demands, complexity, cost, and/or the like.

BRIEF DESCRIPTION OF THE DRAWINGS

Claimed subject matter is particularly pointed out and distinctly claimed in the concluding portion of the specification. However, both as to organization and/or method of operation, together with objects, features, and/or advantages thereof, it may best be understood by reference to the following detailed description if read with the accompanying drawings in which:

Figure 1:
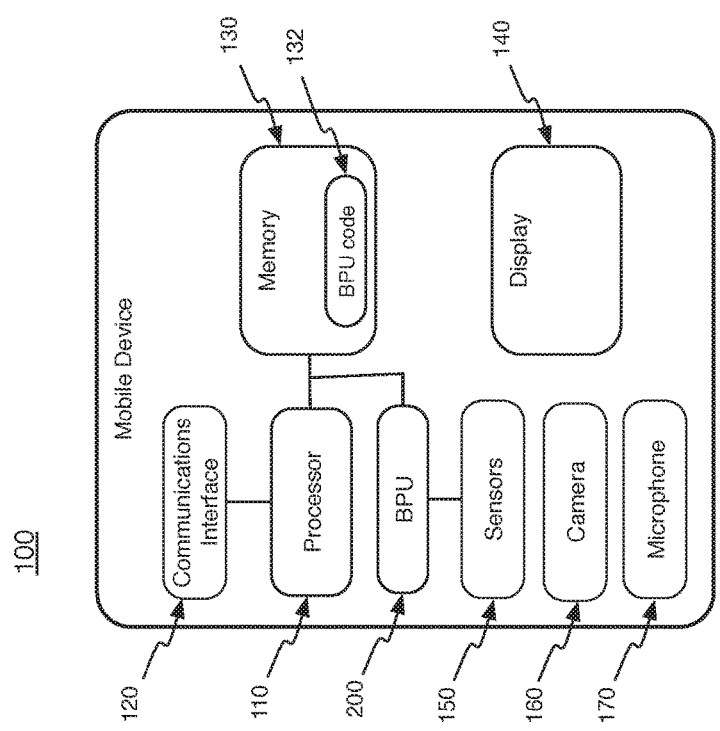
FIG. 1 is an illustration of an example mobile device, in accordance with an embodiment.

Reference is made in the following detailed description to accompanying drawings, which form a part hereof, wherein like numerals may designate like parts throughout that are corresponding and/or analogous. It will be appreciated that the figures have not necessarily been drawn to scale, such as for simplicity and/or clarity of illustration. For example, dimensions of some aspects may be exaggerated relative to others. Further, it is to be understood that other embodiments may be utilized. Furthermore, structural and/or other changes may be made without departing from claimed subject matter. References throughout this specification to "claimed subject matter" refer to subject matter intended to be covered by one or more claims, or any portion thereof, and are not necessarily intended to refer to a complete claim set, to a particular combination of claim sets (e.g., method claims, apparatus claims, etc.), or to a particular claim. It should also be noted that directions and/or references, for example, such as up, down, top, bottom, and so on, may be used to facilitate discussion of drawings and are not intended to restrict application of claimed subject matter. Therefore, the following detailed description is not to be taken to limit claimed subject matter and/or equivalents.

DETAILED DESCRIPTION

References throughout this specification to one implementation, an implementation, one embodiment, an embodiment, and/or the like means that a particular feature, structure, characteristic, and/or the like described in relation to a particular implementation and/or embodiment is included in at least one implementation and/or embodiment of claimed subject matter. Thus, appearances of such phrases, for example, in various places throughout this specification are not necessarily intended to refer to the same implementation and/or embodiment or to any one particular implementation and/or embodiment. Furthermore, it is to be understood that particular features, structures, characteristics, and/or the like described are capable of being combined in various ways in one or more implementations and/or embodiments and, therefore, are within intended claim scope. In general, of course, as has always been the case for the specification of a patent application, these and other issues have a potential to vary in a particular context of usage. In other words, throughout the patent application, particular context of description and/or usage provides helpful guidance regarding reasonable inferences to be drawn; however, likewise, "in this context" in general without further qualification refers to the context of the present patent application.

As mentioned, integrated circuit devices, such as processors, for example, may be found in a wide range of electronic device types. For example, one or more processors may be used in mobile devices, such as cellular phones, for example, as well as in computers, digital cameras, tablet devices, personal digital assistants, wearable devices, etc. Mobile devices and/or other computing devices, for example, may include integrated circuit devices, such as processors, to process signals and/or states representative of a diverse of content types for a variety of purposes. With an abundance of diverse content being accessible, signal and/or state processing techniques continue to evolve. At times, however, processing signals and/or states representative of diverse content may prove to be relatively resource-demanding, which may present a number of challenges including, for example, increased processing time, storage demands, complexity, cost, and/or the like.

In an embodiment, content, such as behavioral profile content for a particular user, may be tracked, wherein the behavioral profile content may include a plurality of parameters representative of a current behavioral state or biological state, or a combination thereof, of the particular user. Tracked signals and/or states representative of the behavioral content may be stored in at least one memory. Further, an embodiment may include determining, at least in part via at least one processor performing one or more machine learning operations, one or more relationships between the tracked behavioral profile content and bioavailability or balance, or a combination thereof, of one or more particular substances within a particular user's body. An embodiment may further include generating, at least in part via at least one processor, one or more recommendations for supplementation related to particular one or more substances for a particular user, wherein one or more recommendations may be directed to improvement of a subsequent state of a particular user. Of course, these are merely examples of how behavioral profile content may be processed and/or otherwise utilized, and subject matter is not limited in scope in these respects.

In an embodiment, content obtained from one or more sensors may be processed by particular hardware circuitry to generate behavioral profile content representative of a particular operator's physical, mental, and/or emotional state. For example, a processor, such as a behavioral processing unit, may be dedicated, at least in part, to processing sensor content to generate behavioral profile content representative of a particular operator's physical, mental, and/or emotional state. A processor, such as a behavioral processing unit, may include particular circuitry directed to performing particular operations to relatively more efficiently process sensor content to generate behavioral profile content for a particular operator, in an embodiment. For example, in an embodiment, a processor, such as a behavioral processing unit, may include machine learning acceleration circuitry directed to performing particular operations that may relatively more efficiently operate on sets of parameters, such as multi-dimensional sets of parameters, that may be utilized in various machine learning techniques such as, for example, neural networks, as discussed more fully below. In an embodiment, a processor, such as a behavioral processing unit, may comprise a co-processor, for example, that may operate in cooperation with a general-purpose processor, although claimed subject matter is not limited in this respect.

The terms "operator" and/or "user" refers to human individuals, and/or may be utilized herein interchangeably. In an embodiment, an operator and/or user may operate a machine, although subject matter is not limited in scope in these respects. Further, as utilized herein, "machine" refers to an article of manufacture, such as, for example, a mechanically, electrically, and/or electronically operated device for performing a task. In some embodiments, operation of a machine may be performed by a combination of an operator and/or a computing device, and/or operation of a machine may be based at least in part on a behavioral profile of at least one particular operator, as explained more fully herein.

As utilized herein, "behavioral profile content" and/or the like refers to one or more parameters representative of a current behavioral state or biological state, or a combination thereof, for at least one particular operator. Thus, for example, "behavioral profile content" and/or the like is not limited to merely behavioral aspects of a particular operator's current state, but may also include parameters representative of one or more biological aspects with respect to a particular operator, as explained more fully herein. Further, although some embodiments herein may be described in connection with "a" user and/or "a" particular user, subject matter is not limited to a single user. For example, at least some embodiments may include behavioral profile content for one or more users, although, again, claimed subject matter is not limited in scope in these respects.

Further, as utilized herein, the term "current" and/or the like refers to substantially and/or approximately current with respect to a point in time. For example, a "current" behavioral and/or biological state of a particular user refers to a behavioral and/or biological state for the particular user derived at least in part from relatively recent sensor content. For example, in an embodiment, behavioral profile content for a particular user may be representative of a behavioral and/or biological state of the particular user derived at least in part from sensor content obtained from one or more sensors within fractions of a second of being generated.

FIG. 1 is an illustration of an embodiment 100 of an example mobile device. In an embodiment, a mobile device, such as 100, may comprise one or more processors, such as processor 110 and/or behavioral processing unit (BPU) 200, and/or may comprise one or more communications interfaces, such as communications interface 120. In an embodiment, one or more communications interfaces, such as communications interface 120, may enable wireless communications between a mobile device, such as mobile device 100, and one or more other computing devices. In an embodiment, wireless communications may occur substantially in accordance any of a wide range of communication protocols, such as those mentioned herein, for example.

In an embodiment, a mobile device, such as mobile device 100, may include a memory, such as memory 130. In an embodiment, memory 130 may comprise a non-volatile memory, for example. Further, in an embodiment, a memory, such as memory 130, may have stored therein executable instructions, such as for one or more operating systems, communications protocols, and/or applications, for example. A memory, such as 130, may further store particular instructions, such as BPU code 132, executable by a behavioral processing unit, such as 200, to generate, at least in part, behavioral profile content. Further, in an embodiment, a mobile device, such as mobile device 100, may comprise a display, such as display 140, one or more sensors, such as one or more sensors 150, one or more cameras, such as one or more cameras 160, and/or one or more microphones, such as microphone 170, for example.

Although BPU 200 is described as executing instructions, such as BPU code 132, other embodiments of behavioral processing units may not fetch and execute code. In an embodiment, a behavioral processing unit may include dedicated and/or specialized circuitry for processing sensor content and/or for generating behavioral profile content, as described more fully below.

As utilized herein, "sensors" and/or the like refer to a device and/or component that may respond to physical stimulus, such as, for example, heat, light, sound pressure, magnetism, particular motions, etc., and/or that may generate one or more signals and/or states in response to physical stimulus. Thus, although camera 160 and/or microphone 170 are depicted in FIG. 1 as separate from sensors 150, the term "sensor" and/or the like may include microphones and/or cameras, in an embodiment. Example sensors may include, but are not limited to, one or more accelerometers, gyroscopes, thermometers, magnetometers, barometers, light sensors, proximity sensors, hear-rate monitors, perspiration sensors, hydration sensors, breath sensors, etc., and/or any combination thereof. In an embodiment, one or more sensors may monitor one or more aspects of a particular operator's biological and/or behavioral state.

In an embodiment, to generate behavioral profile content for a particular operator, a computing device, such as mobile device 100, may obtain signals and/or states representative of content from one or more sensors, such as one or more of sensors 150, camera 160, and/or microphone 170, or any combination thereof. Also, in an embodiment, a processor, such as behavioral processing unit 200, may process sensor content, such as content from one or more of sensors 150, camera 160, and/or microphone 170, or any combination thereof, to generate behavioral profile content for a particular user. In an embodiment, a processor, such as behavioral processing unit 200, may include behavioral content processing circuitry. For example, a processor, such as behavioral processing unit 200, may include machine learning acceleration circuitry, in an embodiment.

For example, a processor, such as behavioral processing unit 200, may include one or more arithmetic units directed to operations involving relatively larger parameter sets, such as parameter sets that may be employed in machine learning, such as neural networks. In an embodiment, machine learning acceleration circuitry, such as arithmetic units directed to operations involving neural network parameter sets and/or other relatively larger parameter sets, for example, may be utilized to process sensor content to generate behavioral profile content for a particular operator. In an embodiment, behavioral profile content may be utilized to affect operation of a particular machine, to generate recommendations for a particular user directed to the particular user's behavioral and/or biological state, to generate customized content for consumption by the particular user, etc., to name but a few non-limiting examples.

In an embodiment, a general-purpose processor, such as processor 110, and a behavioral processing unit, such as 200, may comprise separate integrated circuit devices. In other embodiments, a general-purpose processor, such as processor 110, and a behavioral processing unit, such as 200, may be formed on the same integrated circuit die and/or integrated circuit package. Further, in an embodiment, a processor, such as behavioral processing unit 200, may comprise a co-processor that may operate in cooperation with a general purpose processor, such as 110. For example, a processor, such as 110, may execute code comprising operating systems, applications, etc. Also, in an embodiment, a behavioral processing unit, such as 200, may perform operations dedicated to generating behavioral profile content for one or more operators. For example, a behavioral processing unit, such as 200, may include circuitry for relatively more efficiently executing particular instructions and/or instructions sets, such as code 132, for operating on relatively larger parameters sets, such as may be utilized in connection with particular machine learning techniques, including, for example, neural networks.

In an embodiment, behavioral profile content, such as may be generated by a behavioral processing unit, such as 200, may be communicated between a behavioral processing unit, such as 200, as any of a wide range of devices, systems, and/or processes. For example, behavioral profile content generated by behavioral processing unit 200 may be stored in a memory, such as 130, and/or may be pushed and/or otherwise made available to processor 110 and/or to other devices and/or systems. In an embodiment, behavioral profile content may be communicated via one or more wired and/or wireless communication networks between a computing device, such as mobile device 100, and one or more other network devices, such as one or more other computing devices. Of course, subject matter is not limited in scope in these respects.

In an embodiment, behavioral profile content may include a particular specified set of parameters representative of a particular operator's behavioral and/or biological state that may be utilized, at least in part, by any of a wide range of devices, systems, and/or processes for any of a wide range of applications and/or purposes. In an embodiment, by generating a specified set of parameters comprising behavioral profile content, other devices, systems, applications, and/or processes, for example, may be relieved of responsibility for generating behavioral profile content and may, instead, concentrate on particular areas of expertise and/or specialization. For example, application developers may design applications to take advantage of one or more parameters of behavioral profile content for one or more particular users without having to incur the costs (time, money, resources, etc.) of developing circuitry, code, etc. for gathering and/or processing sensor content and/or for generating behavioral profile content.

Although FIG. 1 depicts an embodiment of a mobile device, such as mobile device 100, other embodiments may include other types of computing devices. Example types of computing devices may include, for example, any of a wide range of digital electronic devices, including, but not limited to, desktop and/or notebook computers, high-definition televisions, digital video players and/or recorders, game consoles, satellite television receivers, cellular telephones, tablet devices, wearable devices, personal digital assistants, mobile audio and/or video playback and/or recording devices, or any combination of the foregoing.

Figure 2:
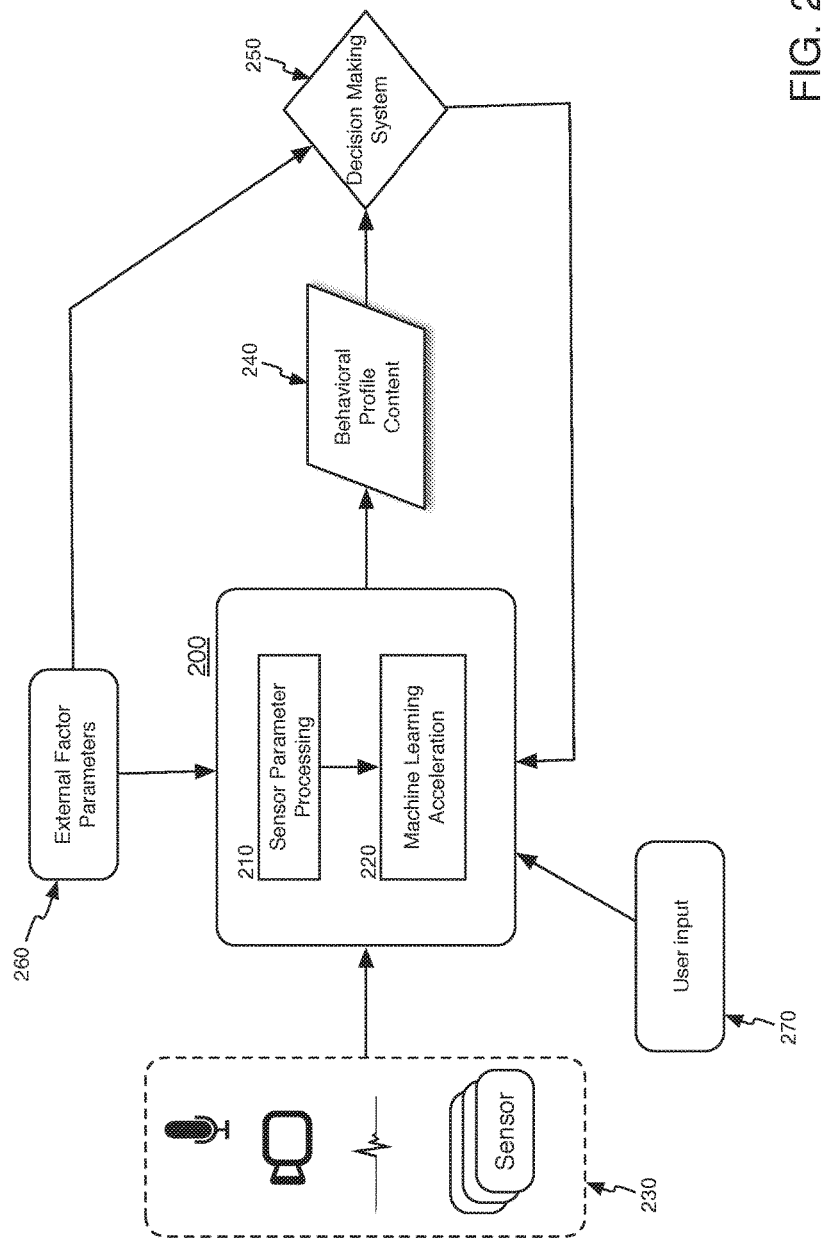
FIG. 2 is an illustration of an example processor for processing signals and/or states representative of behavioral content in a computing device, in accordance with an embodiment.

FIG. 2 is an illustration of an embodiment 200 of an processor, such as a behavioral processing unit, to process signals and/or states representative of behavioral content in a computing device. In an embodiment, to generate behavioral profile content, such as behavioral profile content 240, for a particular user, a processor, such as behavioral processing unit 200, may obtain signals and/or states representative of content from one or more sensors, such as one or more of sensors 230. Also, in an embodiment, a processor, such as behavioral processing unit 200, may process sensor content, such as content from one or more of sensors 230, to generate behavioral profile content, such as behavioral profile content 240, for a particular user. In an embodiment, a processor, such as behavioral processing unit 200, may include behavioral content processing circuitry. For example, a processor, such as behavioral processing unit 200, may include sensor parameter processing circuitry, such as circuitry 210, and/or may include machine learning acceleration circuitry, such as circuitry 220, in an embodiment.

In an embodiment, a processor, such as behavioral processing unit 200, may provide circuitry to generate, at least in part, behavioral profile content, such as behavioral profile content 240, for a particular user to be utilized for any of a wide range of possible applications, such as example applications described herein. For example, in an embodiment, behavioral profile content may be provided to a decision-making device, process, and/or system, such as decision-making device, system, and/or process 250. In an embodiment, a processor, such as behavioral processing unit 200, may relatively more efficiently process signals and/or states obtained from one or more behavioral, biological, and/or environmental sensors, or a combination thereof, associated with a particular user and/or a particular environment, for example. In an embodiment, a processor, such as behavioral processing unit 200, may calculate probabilities for "hidden" (e.g., emotional and/or biological) states of a particular operator at least in part by generating behavioral profile content, such as behavioral profile content 240, that may be utilized by one or more devices, systems, and/or processes, such as decision-making device, system, and/or process 250, for any of a wide range of possible purposes.

For example, as mentioned, behavioral profile content for a particular user may be tracked, wherein the behavioral profile content may include a plurality of parameters representative of a current behavioral state or biological state, or a combination thereof, of the particular user. Further, in an embodiment, one or more relationships between tracked behavioral profile content and bioavailability or balance, or a combination thereof, of one or more particular substances within a particular user's body may be determined, for example. An embodiment may further include generating one or more recommendations for supplementation related to particular one or more substances for a particular user, wherein one or more recommendations may be directed to improvement of a subsequent state of a particular user. Of course, claimed subject matter is not limited in scope in these respects.

In an embodiment, machine-based decision-making, such as decision-making device, system, and/or process 250, based at least in part on behavioral profile content, may, for example, include dynamic recommendation of supplementation related to particular one or more substances for a particular user with a goal of improving a current and/or subsequent state of the particular user. In an embodiment, sensor content may comprise content from any of a wide range of possible sources and/or that may be variable. In an embodiment, a processor, such as a behavioral processing unit, may incorporate machine-learning (e.g., neural networks, etc.) at least in part to adapt to the presence and/or absence of one or more particular sensors while providing probabilities, for example, represented at least in part by behavioral profile content.

In an embodiment, machine-based decision-making, such as may be performed by decision-making device, system, and/or process 250, for example, may depend at least in part on a user's current state and/or the user's ability to relatively quickly respond to changes in the user's state. A wide range of possible sensor types may provide content representative of various aspects of a particular operator's biological and/or behavioral state, and/or representative of one or more environmental factors and/or other external factors. In an embodiment, a processor, such as behavioral processing unit 200, may include a sensor parameter processing unit, such as sensor parameter processing unit 210. In an embodiment, a sensor parameter processing unit, such as sensor parameter processing unit 210, may obtain signals and/or states from one or more sensors, such as sensors 230, and/or may process signals and/or states from one or more sensors to combine, coordinate, normalize and/or otherwise condition signals and/or states from one or more sensors.

For example, a sensor parameter processing unit, such as sensor parameter processing unit 210, may prepare sensor content for further processing, such as via machine learning operations. In an embodiment, machine learning acceleration circuitry, such as machine learning acceleration circuitry 220, may, at least in part, process sensor content to infer a substantially current biological and/or behavioral state of a particular operator. For example, a camera sensor and/or the like may provide one or more signals and/or states to a sensor parameter processing unit, such as sensor parameter processing unit 210. Sensor parameter processing unit 210 may generate one or more parameters representative of pupil dilation, focal point, blink duration, and/or blink rate, or any combination thereof, for example.

In an embodiment, machine learning acceleration circuitry, such as machine learning acceleration circuitry 220, may generate, at least in part, a representation of a particular operator's biological and/or behavioral state, such as behavioral profile content 240. In an embodiment, behavioral profile content, such as behavioral profile content 240, may comprise a specified set of parameters that may be utilized by any of a wide range of machine-based (e.g., computing device-based) decision making systems, devices, and/or processes, such as decision-making device, system, and/or process 250. In an embodiment, behavioral profile content may include a plurality of parameters representative of focal point, excitement, anger, fear, fatigue, dehydration, or focus/distraction, or any combination thereof, in relation to a particular user. Behavioral profile content may further include, by way of additional non-limiting examples, parameters representative of pre-breakthrough, silent like, regret/error acknowledgment, hunger, sloppiness/precision, empathy, and/or social engagement level, or any combination thereof.

In an embodiment, behavioral profile content may comprise a specified set of parameters, such as at least a subset of those mentioned above, for example. In an embodiment, a processor, such as behavioral processing unit 200, may generate a set of parameters representative of behavioral profile content specified in a manner so as to provide content regarding a particular user's behavioral and/or biological state to any of a wide range of devices, systems, and/or processes for any of a wide range of purposes and/or applications. Further, such a set of specified behavioral profile content parameters may be utilized concurrently by any number of devices, systems, and/or processes.

In an embodiment, a processor, such as behavioral processing unit 200, may repetitively obtain sensor content and/or may repetitively generate behavioral profile content for a particular user. For example, sensor content may be gathered and/or otherwise obtained at regular and/or specified intervals, and/or behavioral profile content may be generated at regular and/or specified intervals. In an embodiment, one or more devices, systems, and/or processes may track behavioral profile content over a period of time, for example, such as to detect changes in behavioral profile content, for example.

In an embodiment, a processor, such as behavioral processing unit 200, may be advantageously utilized at least in part by dedicating computing resources to process sensor content, for example, and/or to generate behavioral profile content, such as 240, for a particular user. Further, by generating a specified set of parameters comprising behavioral profile content, such as 240, systems, devices, and/or processes may be relieved of responsibility for generating behavioral profile content and may, for example, concentrate on particular areas of expertise and/or specialization, for example. Further, development costs may be reduced for systems, devices, and/or processes at least in part due to having a specified set of behavioral profile content parameters available from a processor, such as behavioral processing unit 200.

In an embodiment, a processor, such as behavioral processing unit 200, may merge substantially real-time sensor content (e.g., behavioral and/or biological sensor content, or a combination thereof) with representations of prior relationships (e.g., known and/or determined connections between that which may be measured and/or human states). Also, in an embodiment, a processor, such as behavioral processing unit 200, may utilize machine learning techniques (e.g., neural networks, etc.) to map incoming sensor content representative of one or more aspects of an operator's biological and/or behavioral state. In an embodiment, a processor, such as behavioral processing unit 200, may include support for relatively more efficient coordination and/or processing of content obtained from a wide range of possible sources (e.g., combination of content from biological and/or behavioral sensors and/or content representative of other factors) to generate a specified set of parameters, such as behavioral profile content 240. Further, in an embodiment, one or more memory devices may be provided to store operator-dependent and/or operator-independent content to enable relatively quicker identification of state changes in a particular user.

In an embodiment, machine learning operations such as may be performed by a processor, such as behavioral processing unit 200, for example, may store user-specific content in one or more memory devices and/or may also store user-generic content (e.g., determined and/or substantially known relationships between sensor content and/or user states). In an embodiment, user-specific content and/or user-generic content may be processed, such as via machine learning operations, to generate one or more output state vectors, such as behavioral profile content 240.

In an embodiment, external factors may come in to play with respect to generating behavioral profile content and/or decision-making. For example, one or more parameters indicative of one or more external factors, such as external factor parameters 260, may be obtained by a behavioral profile unit, such as BPU 200, and/or by a decision-making device, system, and/or process, such as decision-making system 250. Parameters representative of external factors may include, for example, parameters representative of location, time of day, presence and/or identity of external individual, and/or general sentiment. Further, in an embodiment, parameters, such as parameters 270, may be obtained from a user. For example, a user may provide input parameters representative of instances of supplementation and/or consumption of a particular substance (e.g., nutritional supplementation, medicines, food, drink, etc.). For example, input parameters 270 may include parameters representative of substance identity, amount, time and/or date of supplementation, etc.

Figure 3:
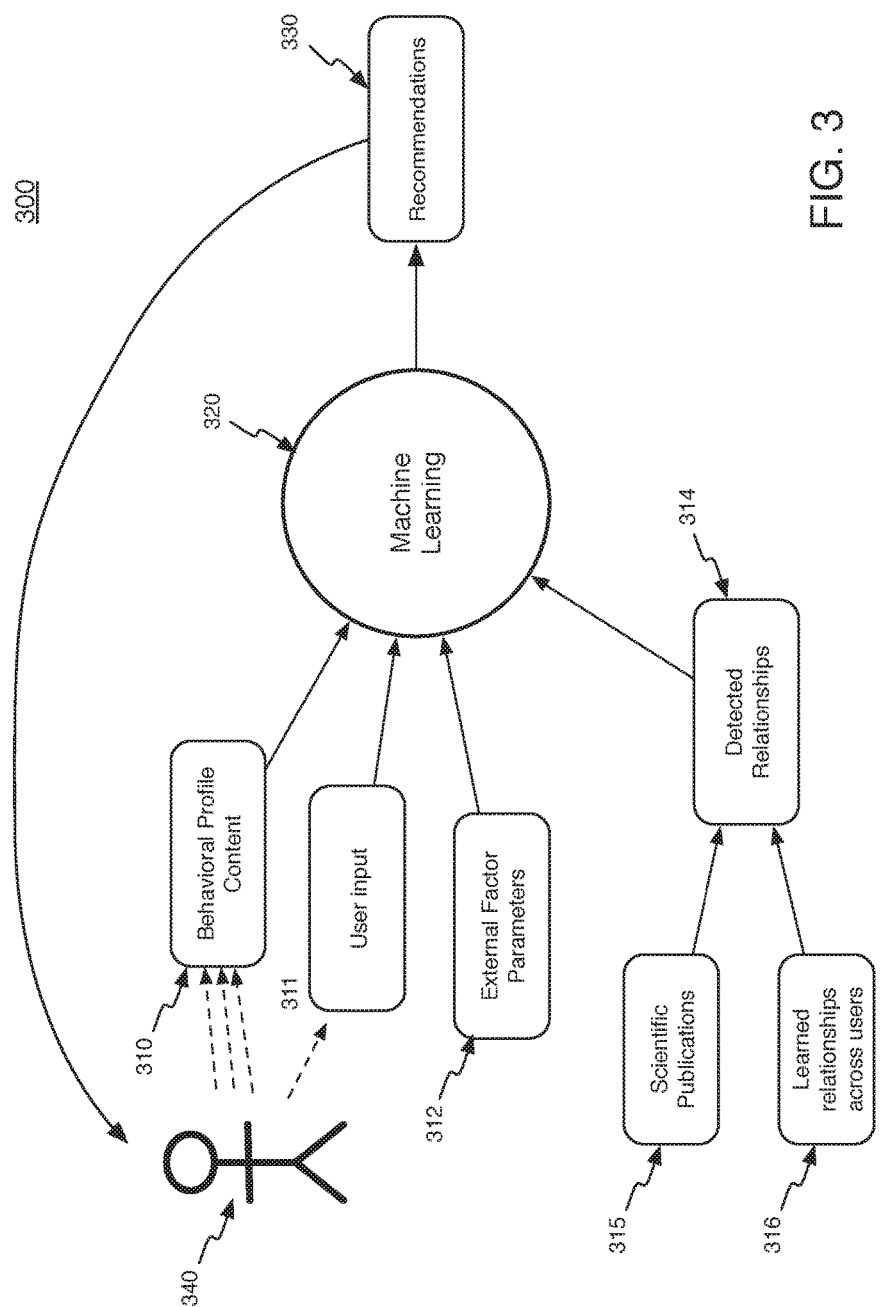
FIG. 3 is an illustration of an example device, system, and/or process for tracking signals and/or states representative of behavioral profile content, in accordance with an embodiment.

FIG. 3 is an illustration of an embodiment 300 of an example device, system, and/or process for processing behavioral profile content, such as behavioral profile content 310, for any of a wide range of possible applications and/or purposes. For example, in an embodiment, behavioral profile content, such as behavioral profile content 310, may be utilized, at least in part, to track one or more relationships between behavioral profile content and bioavailability or balance, or a combination thereof, of one or more particular substances within a particular user's body, for example. An embodiment may further include generating one or more recommendations for supplementation related to one or more particular substances for a particular user, wherein one or more recommendations may be directed to improvement of a current and/or subsequent state of a particular user. For example, in an embodiment, content from one or more cameras pointed at a user's eyes, a microphone, a skin sensor to measure perspiration and/or temperature, one or more pressure sensors for the user's fingers, a heart rate monitor, a hydration sensor, and/or a breath monitor, or any combination thereof, may be utilized as part of a supplementation recommendation system.

In an embodiment, a processor, such as behavioral processing unit 200, may obtain content from one or more sensors, such as one or more sensors mentioned above, and/or may generate a set of parameters, such as behavioral profile content 310, representative of a substantially current biological and/or behavioral state for a particular user. For example, sensor content obtained via a camera, for example, may be processed to generate behavioral profile content, such as behavioral profile content 310, for a particular user, such as user 340, representative of pupil dilation, focal point, blink duration, and/or blink rate, to name a few non-limiting examples. Further, digital audio content, such as may be obtained via a microphone, for example, may be processed to generate behavioral profile content, such as behavioral profile content 310, representative of volume, tone, and/or sentiment, for example.

In an embodiment, determined and/or substantially known relationships, such as relationship parameters 314, may include relationships between behavioral profile content and/or user states and/or may include scientifically determined relationships. In an embodiment, relationships between content that may be gleaned from sensor output and a user's behavioral and/or biological state may be determined, at least in part, via one or more scientific publications, such as scientific publications parameters 315. For example, pupil dilation may be linked with dopamine release according to one or more scientific publications, such from the National Institute of Health (NIH). Further, for example, dopamine release may be linked with anticipation and/or relatively heightened emotional response to stimulus according to one or more scientific studies, such as may be published by Nature research journal. In an embodiment, content representative of relationships gleaned from scientific publications may be stored in at least one memory, such as memory 130, for example, and/or may be provided to a device, system, and/or process for performing machine learning operations, such as depicted at machine learning 320.

In an embodiment, in addition to and/or instead of scientifically determined relationships, other relationships may be determined offline through content collection and/or machine learning. For example, test subjects, such as one or more users, may provide behavioral and/or biological state content and/or may provide biological and/or behavioral marker content so that relationships between such biomarkers and behavioral and/or biological state content may be determined, such as learned relationships parameters 316. In an embodiment, biomarkers may be recorded for test subjects as they are presented with content and/or substances that aim to evoke a particular state, for example. Via machine learning, such as machine learning 320, a variety of behavioral and/or behavioral states for a user may be learned to be identified through biological and/or behavioral markers, in an embodiment.

In an embodiment, a device, system, and/or process, such as machine learning 320, may generate recommendations, such as recommendation parameters 330, based at least in part on behavioral profile content, such as behavioral profile content 310, for a particular user, such as user 340. In this context, "recommendations" refers to one or more indications of suggestions and/or actions that may be taken by one or more individuals, devices, systems, and/or processes at least in part in response to behavioral profile content, such as behavioral profile content 310 and/or user input 311, at least in part in response to external factor parameters, such as parameters 312, and/or at least in part in response to detected relationships, such as detected relationship parameters 314. For example, recommendations, such as recommendation parameters 330, may include suggestions, presented to a particular user, directed to improving one or more aspects of particular user's behavioral and/or biological state. Also, for another example, recommendations, such as recommendation parameters 330, may be directed to supplementation with one or more particular substances.

In another embodiment, behavioral profile content, such as behavioral profile content 310, provided, for example, by a behavioral processing unit, such as behavioral processing unit 200, may be utilized to help manage a user's physical and/or mental health. For example, in an embodiment, relationships between behavioral profile content related to eye movement and a balance of GABA and glutamate neurotransmitters may be tracked, evaluated, and/or learned (e.g., via machine learning). In some circumstances, a human body may attempt to balance GABA, a calming neurotransmitter, with glutamate, an excitatory neurotransmitter. However, in some situations, balance between GABA and glutamate, for example, may be neither immediately and/or perfectly executed. For example, genetic mutations such as GAD1, co-factor availability such as B6, or an increased number of glutamate receptor sites due to excess glutamate in a developing brain may adversely affect GABA/glutamate balance. Glutamate may be involved in learning language processing, sleep, and/or mood, to name a few examples.

In some situations, glutamate may be manipulated by some processed foods, for example, and may not be measured and/or labeled. An overabundance of glutamate may result, which may adversely impact children as the brain is developing, for example. To help address this issue, diets may be restricted and general GABA supplementation may be recommended. However, frequent lab testing may be cost prohibitive. Further, because GABA/glutamate balance may change relatively frequently and/or continuously, it would be infeasible to perform lab testing sufficiently frequently to track such changes. Parents of autistic children, for example, may turn to behavioral monitoring in situations wherein parents may be able to recognize comparatively exaggerated behaviors such as yelling, biting, self-harm, etc. Embodiments that may more readily, efficiently, and/or non-invasively recognize GABA/glutamate imbalance may be advantageously utilized to address issues related to GABA/glutamate imbalance, for example. Also, for example, embodiments may provide for recognition of GABA/glutamate imbalance before behaviors such as yelling, biting, self-harm, etc. become manifest.

In an embodiment, machine learning, such as machine learning 320, may identify changes in GABA/glutamate balance at least in part via tracking of behavioral profile content indicative of eye movement, including parameters indicative of blink duration, eye darting, blinking rate, ability to focus, pupil dilation, etc. In an embodiment, a camera may approximately continuously track a particular user's eye behavior. Content related to need for and/or effect of GABA supplementation may also be tracked. In an embodiment, a device, system, and/or process may learn, such as via machine learning techniques, to identify changes in GABA/glutamate balance based at least in part on eye movement parameters and/or based at least in part on content, such as scientific publication content 315, related to need for and/or effect of GABA supplementation. Further, in an embodiment, recommendations may be generated, such as via machine learning 320, regarding GABA supplementation for a particular user based, at least in part, on identified GABA/glutamate balance changes. Embodiments may help ensure beneficial GABA/glutamate balance, such as for an autistic child at key developmental stages, which may produce improvements in health and/or social capabilities, for example. Further, embodiments may be advantageously utilized for children, students, those with sleep impairments, and/or those with anxiety disorders, for example.

In another embodiment, relationships between behavioral eye content, such as behavioral profile content associated with eye movement, and bioavailability levels of 5-methyltetrahydrafolate (5-MTHF) may be tracked, evaluated, and/or learned, such as via machine learning 320. In some circumstances, a human body may convert dietary and/or supplemental folate into 5-MTHF for use in key biological processes such as, for example, detoxification, epigenetic functioning, and/or neurotransmitter balancing, among others. Approximately 9-11% of the general population, and approximately 98% of the autistic population, may have a genetic mutation that affects conversion of one form of folate to another. Due at least in part to relatively higher consequences of sub-optimal levels of 5-MTHF, it may be beneficial to identify changes in bioavailable 5-MTHF readily and/or efficiently.

In an embodiment, machine-learning, such as machine learning 320, may identify changes in bioavailable 5-MTHF substantially in real-time (i.e., approximately as it is occurring) through monitoring behavioral indicators in eye movement. For example, behavioral profile parameters for a particular user related to eye darting, blinking rate, ability to focus, and/or pupil dilation, for example, may be tracked. Content related to need for and/or effect of 5-MTHF supplementation may also be tracked. In an embodiment, a device, system, and/or process may learn, such as via machine learning techniques, to identify changes in 5-MTHF bioavailability based at least in part on eye movement parameters and/or based at least in part on content, such as scientific publication content 315, related to need for and/or effect of 5-MTHF supplementation.

Further, in an embodiment, recommendations may be generated, such as via machine learning 320, regarding 5-MTHF supplementation for a particular user based, at least in part, on identified 5-MTHF bioavailability changes. In embodiments, changes in bioavailability of 5-MTHF may be identified prior to an individuals' perception that a change has occurred, thereby helping to reduce negative consequences. In an embodiment, an identified change in bioavailability of 5-MTHF and/or a recommendation for supplementation of 5-MTHF may be communicated to a caretaker for a particular user. This may be advantageous, for example, in situations wherein an effected individual may be unable to communicate or comprehend the change, such as may be situation in the case of autism. Further, embodiments may help address, at least in part, the infeasibility of continuous lab testing, and/or may help parents of autistic children, for example, to pre-emptively avoid relatively higher-consequence behaviors (e.g., yelling, biting, self-harm, etc.). Parents of autistic children, for example, may perform behavioral monitoring, but may tend to notice relatively more extreme behaviors. Embodiments may allow for correlation of more subtle behaviors, such as eye movements, voice characteristics, etc., that may occur before more consequential behaviors manifest. Further, embodiments may provide early identification of a need for supplementation.

In an additional embodiment, machine-learning, such as machine learning 320, may identify changes in bioavailable 5-MTHF substantially in real-time through monitoring behavioral profile parameters related to voice and/or speech. For example, behavioral profile parameters for a particular user related to voice tonality, sentiment analysis, volume, frequency, pitch, timbre, etc., for example, may be tracked. In an embodiment, a microphone may be utilized to approximately continuously track behavioral profile parameters related to voice and/or speech, for example. In an embodiment, a user may be provided with a given paragraph to read aloud and/or may be provided with subjective questions to answer, such as "how was your day?" Voice content gathered from a user reading and/or answering in this manner may be utilized, at least in part, to track voice and/or speech parameters and/or to identify changes in 5-MTHF bioavailability. In another embodiment, voice characteristics may be monitored via a substantially always-on microphone. Such an alternative may have particular value for individuals unwilling and/or unable, such as may be the situation in the case of autism, to interact verbally in an explicit manner.

As mentioned, content related to need for and/or effect of 5-MTHF supplementation may also be tracked. In an embodiment, a device, system, and/or process may learn, such as via machine learning techniques, to identify changes in 5-MTHF bioavailability based at least in part on voice and/or speech-related parameters and/or based at least in part on content, such as scientific publication content 315, related to need for and/or effect of 5-MTHF supplementation. Further, as mentioned, recommendations may be generated, such as via machine learning 320, regarding 5-MTHF supplementation for a particular user based, at least in part, on identified 5-MTHF bioavailability changes.

In another embodiment, machine learning, such as machine learning 320, may be employed at least in part to identify glutamate/GABA manipulation. For example, glutamate/GABA manipulation may be identified based, at least in part, on behavioral profile content for a particular user and/or based, at least in part, on location content such as may be provided, for example, via one or more satellite positioning systems, such as GPS. As mentioned, glutamate is an excitatory neurotransmitter. For this reason, in some situations, food science may be aimed to increase excitation by increasing glutamates (e.g., monosodium glutamate). Information on glutamate levels in foods may be difficult to obtain. Food labels, for example, may recite "seasonings", "spices," and/or "natural flavors" with no actual measurements with respect to glutamates. Further, as mentioned, potentially adverse consequences related at least in part to excess glutamate levels may include sleep impairments, anxiety, and/or inability to focus, for example, and may have relatively higher adverse consequences in a developing brain (e.g., increase in the number of glutamate receptor sites).

In an embodiment, a behavior processing unit, such as BPU 200, and/or a machine learning device, system, and/or process, such as machine learning 320, may identify locations where glutamate/GABA balance may be manipulated. Content indicative of locations where glutamate/GABA balance may be manipulated may be communicated to individuals, thereby allowing individuals and/or caretakers to avoid such locations. Avoiding over-excitation in this pathway may be helpful to those with anxiety disorders. Glutamate/GABA balance may also generally be of interest to those trying to learn new things (e.g., students) and/or to those who may be sensitive (e.g., those having trouble sleeping, autistic children, etc.). For example, a behavior processing unit, such as BPU 200, and/or a machine learning device, system, and/or process, such as machine learning 320, may identify changes in glutamate/GABA balance for one or more individuals over a period of time, for example, and may track parameters indicative of locations at which balance changes occurred. In an embodiment, at least in part in response to identifying a change in glutamate/GABA balance for a particular individual, a location for the particular individual may be determined and parameters indicative of that location may be stored in a database. Over a period of time, a database of glutamate/GABA balance content and associated location content may be developed. Content from a glutamate/GABA and/or location database may be utilized, at least in part, to identify particular locations where glutamate/GABA imbalances are more likely to occur. For example, particular restaurants may be identified, thereby allowing users and/or caretakers to avoid such locations, in an embodiment. Embodiments may provide a relatively efficient and/or non-invasive technique for identifying glutamate manipulation.

To gather location content associated with glutamate/GABA balance changes, an individual may wear a bracelet and/or other wearable device that may track location and/or time spent at a location. In an embodiment, a wearable may include a GPS receiver and/or terrestrial wireless network transmitter, for example. Further, in an embodiment, a machine-learning device, system, and/or process, such as machine learning 320, may be trained at least in part via a user, such as a parent and/or caretaker, for example, providing input, such as user input 311, indicating evidence of over-excitation (e.g., inability to focus) of a particular user. Patterns related to relatively higher-glutamate states and/or their likely sources (e.g., locations) may be learned at least in part via a machine-learning device, system, and/or process, such as machine learning 320, in an embodiment. For example, in a situation wherein a soccer coach may provide relatively higher-glutamate sports drinks at soccer practice, a parent may be identified of an otherwise difficult-to-identify source of glutamate. In a further embodiment, eye behavior may be tracked to, at least in part, identify relatively higher glutamate states rather than and/or in addition to user-provided content identifying particular behavioral states.

Further, in an embodiment, content obtained from wearable sensors, sensors from mobile devices, and/or other sensors may be collected and/or stored over a period of time for one or more users to identify, at least in part, behavioral patterns that may be associated with depressive symptoms. In an embodiment, wearable devices, phones, and/or other devices may include a behavioral processing unit, such as BPU 200, and/or may include one or more devices, systems, and/or processes for machine learning, such as 320, to generate and/or analyze behavioral profile content and/or to generate location content.

Embodiments may also include a device, system, and/or process for machine learning, such as machine learning 320, to identify, at least in part, changes in hormone balance (e.g., testosterone, estrogen, progesterone, etc.) substantially in real-time based, at least in part, on monitored and/or tracked environmental noise. Scientific publications have identified correlations between hormone levels and brain functioning, for example, as well as correlations between hormone levels and an ability to perform tasks involving fine motor skills. In an embodiment, patterns of minor impairments indicative of hormonal imbalance may be identified through environmental sound monitoring, such as via a microphone that may be substantially and/or significantly always-on. In an embodiment, a microphone may be provided by a mobile device, for example. Impairments indicative of hormonal imbalance may be individually of relatively lower consequence, and therefore it may be difficult for an individual to draw inferences and/or conclusions in isolation. However, such impairments, such as may be identified, at least in part, via microphone sensor content, for example, may be identified as a group to be attributed to hormonal imbalance. For example, sounds related to cooking dinner every night may vary with hormonal balance. Sounds associated with hormonal imbalance include indications of clumsiness, erratic movements, dropping things, minor burns while cooking, etc., for example.

In an embodiment, a microphone may be utilized, at least in part, to substantially continuously track environmental sounds associated with a particular user. Content, such as parameters 315 obtained from scientific journals, related to need for and/or effect of supplementation may additionally be tracked. In an embodiment, a device, system, and/or process may learn, such as via machine learning techniques, to identify a need for supplementation based at least in part on monitored environmental sounds and/or based, at least in part, on content obtained from scientific journals and/or other scientific sources. Embodiments may further recommend supplementation of one or more particular substances to a user based at least in part on identified changes in hormonal balance, in an embodiment.

Figure 4:
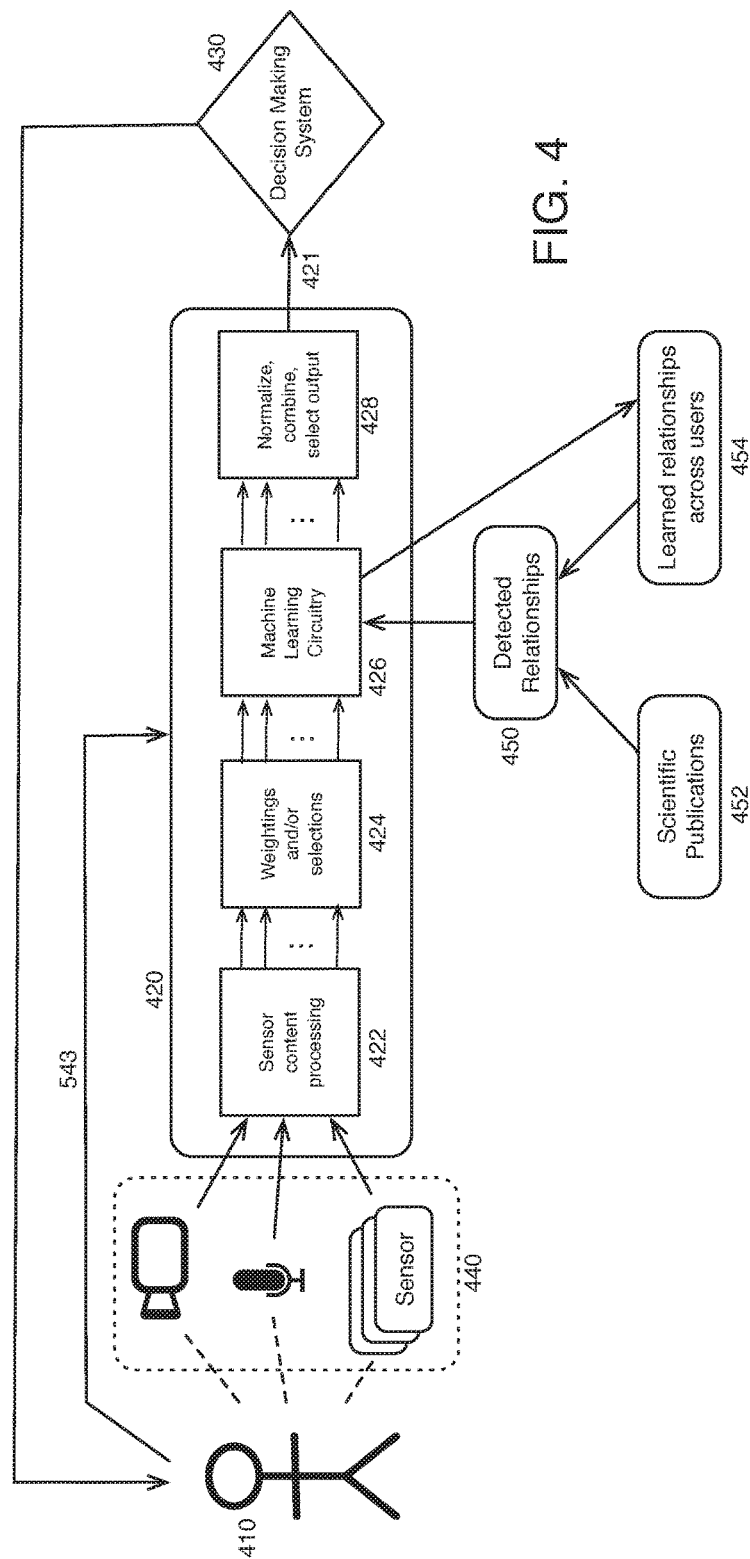
FIG. 4 is an illustration of an example device, system, and/or process for processing signals and/or states representative of behavioral profile content, in accordance with an embodiment.

FIG. 4 is an illustration of an embodiment 400 of a system, including a processor, such as a behavioral processing unit 420, to process signals and/or states representative of behavioral content in a computing device. In an embodiment, to generate behavioral profile content, such as behavioral profile content 421, for a particular user, such as user 410, a processor, such as behavioral processing unit 420, may obtain signals and/or states representative of content from one or more sensors, such as one or more of sensors 440. Also, in an embodiment, a processor, such as behavioral processing unit 420, may process sensor content, such as content from one or more of sensors 440, to generate behavioral profile content, such as behavioral profile content 421, for a particular user. In an embodiment, a processor, such as behavioral processing unit 420, may include behavioral content processing circuitry. For example, a processor, such as behavioral processing unit 420, may include sensor content processing circuitry, such as circuitry 422, and/or may include machine learning circuitry, such as circuitry 424 and/or 426, in an embodiment. In an embodiment, a processor, such as BPU 420, may further obtain content from sensors, such as sensors 440, to track one or more environmental aspects (e.g., environmental sound, temperature, barometric pressure, altitude, location, etc.).

In an embodiment, a processor, such as behavioral processing unit 420, may provide circuitry to generate, at least in part, behavioral profile content, such as behavioral profile content 421, for a particular user, such as user 410, to be utilized for any of a wide range of possible applications and/or purposes. For example, a processor, such as behavioral processing unit 420, may generate behavioral profile content, such as behavioral profile content 421, to, at least in part, to identify imbalances of particular substances within a human body, for example. In an embodiment, behavioral profile content, such as behavioral profile content 421, may include one or more parameters indicative of eye movement, voice and/or speech aspects, environmental sounds, etc. Of course, subject matter is not limited in scope in these respects.

In an embodiment, one or more sensors, such as sensors 440, may provide content representative of various aspects of a particular operator's biological and/or behavioral state, and/or representative of one or more environmental factors and/or other external factors. In an embodiment, sensors 440 may include one or more sensors of one more sensor types, as previously mentioned. Further, in an embodiment, a processor, such as behavioral processing unit 420, may include circuitry, such as circuitry 422, to process content obtained from one or more sensors, such as sensors 440. In an embodiment, content obtained from sensors, such as sensors 440, may include digital signals and/or states, analog signals and/or states, or any combination thereof. For example, circuitry 422 may include digital circuitry, analog circuitry, or a combination thereof. In an embodiment, sensor content processing circuitry, such as circuitry 422, may convert one or more analog signals to digital signals, although subject matter is not limited in scope in this respect. In an embodiment, circuitry, such as circuitry 422, may process signals and/or states from one or more sensors, such as sensors 440, to combine, coordinate, normalize, amplify, filter, and/or otherwise condition signals and/or states from one or more sensors, such as sensors 440, although subject matter is not limited in scope in these respects.

Further, in an embodiment, a processor, such as behavioral processing unit 420, may include circuitry for determining and/or selecting weighting parameters and/or for determining and/or selecting particular machine learning devices, systems, and/or processes. For example, circuitry 424 may determine and/or select one or more particular machine learning techniques, such as one or more particular neural networks and/or including one or more weighting parameters, for example, for use in machine learning operations. In an embodiment, determination and/or selection of weighting parameters and/or machine learning operations, including one or more neural networks, for example, may be based, at least in part, on content, such as parameters 543, identifying one or more aspects of substances consumed by a particular user, such as user 410.

In an embodiment, machine learning circuitry, such as machine learning circuitry 426, may, at least in part, process content, such as may be obtained from circuitry 422 and/or 424, to determine, estimate, and/or infer, for example, one or more parameters representative of a substantially current biological and/or behavioral state of a particular user. In an embodiment, machine learning circuitry, such as machine learning circuitry 426, may generate, at least in part and/or with contribution from output generation circuitry 428, a representation of a particular user's biological and/or behavioral state, such as behavioral profile content 421. In an embodiment, behavioral profile content, such as 421, may include a plurality of parameters representative of focal point, excitement, anger, fear, fatigue, dehydration, or focus/distraction, pre-breakthrough, silent like, regret/error acknowledgment, hunger, sloppiness/precision, empathy, or social engagement level, or any combination thereof, for example. In an embodiment, a processor, such as behavioral processing unit 420, may repetitively and/or substantially periodically obtain sensor content and/or may repetitively and/or substantially periodically generate behavioral profile content, such as behavioral profile content 421, for a particular user, such as user 410. Further, as mentioned, behavioral profile content, such as behavioral profile content 421, may include one or more parameters indicative of voice tonality, voice sentiment, volume, frequency, pitch, timbre, etc. Further, as also mentioned, behavioral profile content, such as behavioral profile content 421, may include one or more parameters representative of eye darting, blinking rate, ability to focus, and/or pupil dilation, to name a few additional non-limiting examples.

In an embodiment, a processor, such as behavioral processing unit 420, may determine appropriate weights for various sensor combinations and/or for particular parameters, such as parameters 415, provided by one or more content providers, such as content provider 405, during offline training operations, for example. In another embodiment, during online operation, for example, a set of inputs may be logged and/or later used as training parameters. For example, a user, such as user 410, may explicitly provide inputs related to supplementation and/or consumption of particular substances and/or may provide inputs related to behaviors indicative of over-excitation and/or indicative of other observed behaviors for a particular individual, for example. Further, in an embodiment, determined and/or substantially known relationships, such as represented by parameters 450, may include relationships between behavioral profile content and/or user states and/or may include scientifically determined relationships. For example, parameters, such as parameters 452, indicative of relationships between content that may be gleaned from sensor output and a user's behavioral and/or biological state may be determined, at least in part, via one or more scientific publications. In an embodiment, parameters, such as parameters 454, representative of other relationships may be determined across multiple users and/or across populations, for example.

Figure 5:
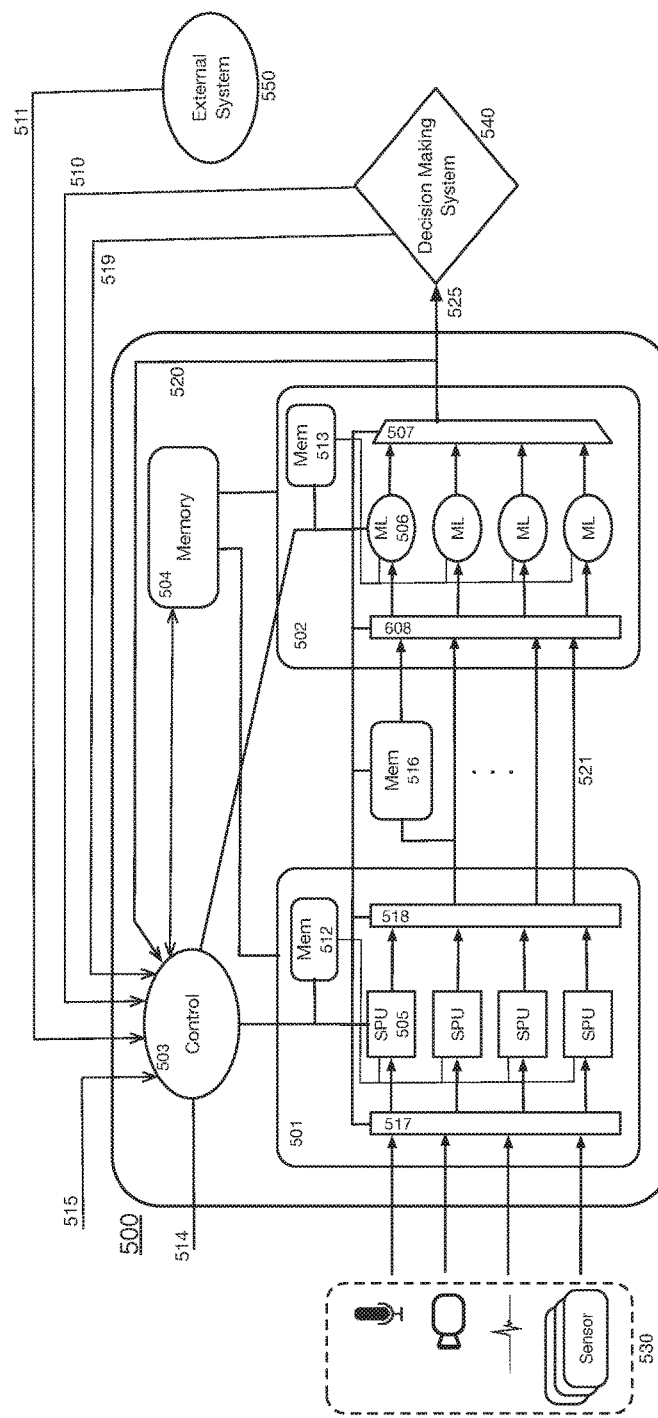
FIG. 5 is a schematic block diagram depicting an example processor for processing signals and/or states representative of behavioral profile content in a computing device, in accordance with an embodiment.

FIG. 5 is a schematic block diagram depicting an embodiment 500 of an example device, such as a behavioral processing unit, for processing content, such as content obtained from sensors 530, to generate signals and/or states representative of behavioral content in a computing device. In an embodiment, a processor, such as behavioral processing unit 500, may process digital signals and/or states or analog signals and/or states, or a combination thereof (e.g., mixed-signal). Any of a wide range of digital and/or analog circuit types may be utilized to process digital, analog, and/or mixed-signal signals and/or states, as explained more fully below. In an embodiment, one or more aspects of a processor, such as behavioral processing unit 500, may be implemented to operate in an analog domain, while one or more other aspects may be implemented to operate in a digital domain. In other embodiments, a processor, such as behavioral processing unit 500, may be implemented to operate substantially wholly in the digital domain and/or the analog domain.

In an embodiment, a processor, such as behavioral processing unit 500, may, in general, substantially continuously obtain content from sensors, such as one or more sensors 530, and/or may substantially continuously generate output signals and/or states, such as behavioral profile content 525. Generated output signals and/or states, such as behavioral profile content 525, may be made available to one or more decision-making systems, such as decision-making system 540, for example. In an embodiment, a decision-making device, system, and/or process, such as decision-making system 540, may determine, at least in part via at least one processor performing one or more machine learning operations, one or more relationships between tracked behavioral profile content, such as behavioral profile content 525 and bioavailability and/or balance, or a combination thereof, of one or more particular substances within a particular user's body. An embodiment may further include a decision-making device, system, and/or process, such as decision-making system 540, to generate one or more recommendations for supplementation related to particular one or more substances for a particular user, wherein one or more recommendations may be directed to improvement of a subsequent state of a particular user.

In an embodiment, a sensor parameter processing stage, such as sensor parameter processing stage 501, may obtain signals and/or states (e.g., digital, analog, and/or mixed-signal) from one or more sensors, such as sensors 530. In an embodiment, a sensor parameter processing stage, such as sensor parameter processing stage 501, may process signals and/or states from one or more sensors at least in part by combining content, adjusting timing, performing noise reductions and/or other signal reduction operations, normalizing content, or any combination thereof, for example. However, claimed subject matter is not limited in scope in this respect.

Further, in an embodiment, sensor content steering circuitry, such as sensor content steering circuitry 517, may direct signals and/or states obtained from sensors, such as from sensors 530, to one or more sensor processing units, such as one or more of sensor processing units (SPU) 505. In an embodiment, sensor processing units, such as SPUs 505, may be configured via one or more control signals, such as control signals communicated between a control unit, such as control unit 503, and sensor processing units, such as SPUs 505. Sensor processing units, such as SPUs 505, may prepare sensor content, such as signals and/or stated obtained from one or more sensors, such as sensors 530, for further processing by, for example, a machine-learning processing stage, such as machine-learning processing stage 502. In an embodiment, sensor content steering circuitry, such as sensor content steering circuitry 517, may direct content based, at least in part, on one or more control signals obtained from a control unit, such as control unit 503, and/or from a memory, such as memory 512, for example.

In an embodiment, a sensor processing stage, such as sensor processing stage 501, may include one or more sensor processing units, such as sensor processing units 505, that may be configured to operate individually or in one or more various combinations. Sensor processing units, such as SPUs 505, may perform, individually and/or in cooperation, any of a variety of operations that may be specified and/or implemented. Such operations may include, for example, combining signals and/or states, adjusting timing of signals and/or states, performing noise reductions and/or other signal reduction operations, and/or normalizing content, to list but a few examples.

One or more sensor processing units, such as SPUs 505, may be implemented to operate in an analog domain and/or one or more units may be implemented to operate in a digital domain. In an embodiment, sensors, such as sensors 530, may provide signals and/or states comprising analog signals and/or comprising digital content (e.g., signals and/or states). Further, in an embodiment, one or more analog signals obtained by one or more sensors, such as 530, may be converted to digital content using analog-to-digital conversion circuitry. In other embodiments, analog signals obtained from sensors, such as sensors 530, for example, may be maintained as analog signals for processing by one or more sensor processing units, such as SPUs 505. Further, in an embodiment, individual sensor processing units, such as SPUs 505, may be implemented in analog and/or digital based, at least in part, on particular tasks to be performed by a particular SPU and/or based, at least in part, on particular signal types to be obtained from sensors, such as sensors 530. In an embodiment, one or more of a variety of filters, signal amplifiers, and/or signal damping circuits, ranging from relatively more simple to relatively more complex, for example, may be performed by one or more particular sensor processing units, such as SPUs 505. Sensor processing unit operations, such as example operations mentioned herein, may have particular relevance in a larger context of behavioral profile content generation in connection with one or more machine-learning units. For example, sensor processing unit operations may be performed with an end-goal of behavioral profile content generation in mind.

In an embodiment, a particular sensor processing unit, such as SPU 505, may include noise reduction, filtering, dampening, combining, amplifying circuitry, etc., for example, implemented to operate in the analog domain. Analog circuitry may include, for example, one or more op-amps, transistors, capacitors, resistors, etc., although claimed subject matter is not limited in scope in this respect. Circuitry, such as noise reduction, filtering, dampening, combining, amplifying circuitry, etc., for example, may also be implemented in the digital domain, or in a combination of analog and/or digital. For another example, a particular sensor processing unit, such as a particular SPU 505, may be implemented in analog and/or digital to combine signals and/or states. In an embodiment, a unit to combine signals and/or states may be implemented in the analog domain or in the digital domain, or a combination thereof. In an embodiment, analog hysteretic "winner-take-all" circuits may be implemented at least in part to improve noise robustness and/or to mitigate, at least in part, timing difference between sensor input streams, for example. Of course, subject matter is not limited in scope in these respects. Further, noise reduction, filtering, dampening, combining, and/or amplifying are merely example tasks that may be performed by one or more sensor processing units, such as SPUs 505, and, again, claimed subject matter is not limited in scope in these respects.

Further, in an embodiment, sensor processing units, such as SPU 505, may be implemented to generate outputs that may exhibit a range of approximation, imprecision, and/or non-replicability. In an embodiment, machine-learning units, such as ML 506, may help mitigate consequences that might otherwise occur due to approximation, imprecision, and/or non-replicability potentially exhibited by sensor processing units, such as SPU 505. As utilized herein, "replicable" in the context of sensor processing units, such as SPU 505, refers to an ability to generate the same output for a given duplicate set of inputs. "Non-replicability" in this context refers to one or more sensor processing units, such as SPU 505, not necessarily generating the same output for a given duplicate set of inputs. That is, in an embodiment, one or more sensor processing units, such as SPU 505, may be implemented in a manner so as to not guarantee similar outputs for similar sets of inputs.

In an embodiment, content steering circuitry, such as content steering circuitry 518, may direct content, such as signals and/or states, generated by one or more sensor processing units, such as SPUs 505, to a machine-learning stage, such as machine-learning stage 502. Content, such as signals and/or states 521, generated by one or more sensor processing units, such as SPUs 505, may also be stored, at least temporarily, in a memory, such as memory 516, for example. In an embodiment, memory 516 may comprise a buffer, such as a first-in, first-out buffer, for example, although claimed subject matter is not limited in scope in this respect. In an embodiment, content steering circuitry, such as content steering circuitry 518, may direct content based, at least in part, on one or more control signals obtained from a control unit, such as control unit 503, and/or from a memory, such as memory 512, for example.

A machine-learning stage, such as machine-learning stage 502, may include content steering circuitry, such as content steering circuitry 508, that may direct content, such as signals and/or states 521, obtained from a sensor processing stage, such as sensor processing stage 501, to one or more machine-learning units (ML), such as machine-learning units 506, for example. In an embodiment, content steering circuitry, such as content-steering circuitry 508, may direct content, such as signals and/or states 521, based, at least in part, on one or more control signals obtained from a control unit, such as control 503, and/or from a memory, such as memory 513.

In an embodiment, machine-learning units, such as machine-learning units 506, may be configured via one or more control signals, such as control signals communicated between a control unit, such as control unit 503, and machine-learning units, such as machine-learning units 506. In an embodiment, one or more machine-learning units, such as machine-learning units 506, may be configured to operate individually or in one combination with one or more other machine-learning units. In an embodiment, individual machine-learning units, such as machine-learning units 506, may implement particular machine-learning techniques. Further, one or more machine-learning units, such as machine-learning units 506, may be implemented to operate in the analog domain or in the digital domain, or a combination thereof. For example, a machine-learning unit operating in the analog domain may include voltage and/or current summing circuits to sum a number of signals and/or states and/or may include devices, such as variable impedance devices, that may apply weighting factors to individual signals and/or states. Of course, claimed subject matter is not limited in scope in these respects.

Content steering/selecting circuitry, such as content steering/selecting circuitry 507, may select and/or combine content generated by one or more machine-learning units, such as machine-learning units 506, in an embodiment. Further, content steering/selecting circuitry, such as content steering/selecting circuitry 507, may direct output, such as signals and/or states representative of behavioral profile content 525, to a decision-making system, such as decision-making system 540. In an embodiment, a control unit, such as control unit 503, may obtain at least a portion of the output generated by machine-learning units, such as machine-learning units 506.

In an embodiment, control unit, such as control unit 503, may configure and/or control one or more aspects of behavioral processing unit 500. In an embodiment, a control unit, such as control unit 503, may obtain inputs from a variety of sources and/or may control various aspects of behavioral processing unit 500 based, at least in part, on the obtained inputs. In an embodiment, control unit inputs may be obtained from units within behavioral processing unit 500 unit itself and/or from one or more other sources. For example, control unit 503 may obtain user parameters 515 (e.g., user ID or other parameters descriptive of a particular user). In an embodiment, user parameters, such as parameters 515, may be obtained from an individual and/or from one or more external sources and/or may be obtained from one or more memories within behavioral processing unit 500. For example, user parameters for one or more particular users may be stored in a memory, such as memory 504.

Various aspects of behavioral processing unit 500 may be configured and/or reconfigured based at least in part on parameters that may be stored on an individual user basis in a memory, such as memory 504. For example, a control unit, such as control unit 503, may communicate with a memory, such as memory 504, to obtain configuration content for a particular user from memory 504, and/or may configure behavioral processing unit 500 based at least in part on the obtained configuration content. Further, in an embodiment, a control unit, such as control unit 503, may obtain content from a decision-making system, such as decision-making system 540, or from one or more external sources, such as external system 550.

Although example behavioral processing unit 500 is depicted having particular memory devices, such as memories 504, 512, 514, and/or 516, other embodiments may include memory elements distributed in various areas of the processing unit. For example, memory elements may be included in one or more sensor processing units 505 and/or in one or more machine-learning units 506. Additionally, a memory, such as memory 504, may be implemented as a hierarchy of memory devices and/or technologies that may allow for various sizes and/or memory access speeds. Further, a memory, such as memory 504, may store machine-learning weighting parameters and/or other machine-learning parameters, and/or may also store control signals, for example.

In an embodiment, a control unit, such as control unit 503, may generate one or more output signals and/or states, such as one or more control signal, based, at least in part, on inputs obtained by the control unit. Control signal output generation may be a function of one or more inputs that may include, for example, user identification parameters, content type parameters, contextual parameters, task parameters, sensor availability parameters, or behavioral profile content specification parameters, or any combination thereof. Of course, these are merely example types of inputs that may be obtained by a control unit, such as control unit 503, and claimed subject matter is not limited in scope to these particular examples.

As mentioned, a control unit, such as control unit 503, may obtain user parameters 515 that may include user identification content and/or other parameters descriptive of a particular user). Further, in an embodiment, a control unit, such as control unit 503, may obtain particular parameters, such as parameters 514, descriptive of substances ingested and/or otherwise consumed by a user (e.g., foods, vitamins, medicines, lotions, creams, cosmetics, soaps, shampoo, etc.). Control unit 503 may further obtain parameters descriptive of a task being performed by a user, or parameters descriptive of context and/or environment, or any combination thereof, for example. In an embodiment, context and/or environmental parameters 511 may be provided by and/or obtained from an external system, such as external system 550. Further, in an embodiment, content and/or task parameters 510 may be provided by and/or obtained from a decision-making system, such as decision-making system 540. For example, parameters descriptive of user/operator and/or task may indicate a type of task being performed (e.g., flying, driving, performing surgery, etc.) and/or may indicate a particular user/operator. Also, for example, parameters descriptive of context and/or environment may indicate a particular setting (e.g., location, time of day, date, etc.), presence of other individuals, or other contextual information, or any combination thereof.

A control unit, such as control unit 503, may also obtain parameters, such as parameters 514, that may be indicative of sensor availability, for example. Additionally, a control unit, such as control unit 503, may obtain parameters, such as parameters 519, that may indicate one or more particular parameters and/or parameter types of behavioral profile content, such as behavioral profile content 525, to be generated on a relative priority basis, for example, by machine-learning stage 502, for example. Further, one or more parameters 520 representative of one or more aspects of behavioral profile content 525 generated by machine-learning stage 502 may be provided to and/or obtained by a control unit, such as control unit 503. For example, parameters 520 may include feedback to control unit 503 that may influence behavioral processing unit operations, in an embodiment.

As mentioned, a control unit, such as control unit 503, may generate one or more control signals based, at least in part, on inputs that may be obtained from any of a range of sources. For example, inputs obtained by control unit 503 may allow for selecting particular content from one or more memory elements, such as one or more of memories 504, 512, 514, and/or 516, to be utilized in configuring sensor processing stage 501 and/or machine-learning stage 502 for processing. For example, sensor processing stage 501 and/or machine-learning stage 502 may be configured based on a particular user/operator, a particular task, or a particular context, or a combination thereof. By tailoring processing in this manner, improved behavioral profile content may be generated, and/or efficiency may be improved (e.g., improved confidence of behavioral profile content while utilizing relatively fewer resources). Further, in an embodiment control unit 503 may steer outputs of sensor processing stage 501 (e.g., intermediary results) to particular machine-learning units 505 via control of steering circuitry 508 based, at least in part, on inputs obtained by control unit 503. Similarly, control unit 503 may select output from one or more particular machine-learning units 506 via control of steering/selecting circuitry 507 based, at least in part, on obtained inputs. Further, weighting of inputs for machine-learning units 506 may be determined at least in part based on obtained inputs. For example, a control unit, such as control unit 503, may steer, select, and/or weight intermediary results (e.g., content generated by sensor processing stage 501) as a function of user/operator identification, task type, environmental context, or sensor availability, or any combination thereof, in an embodiment. Of course, claimed subject matter is not limited in scope in these respects.

Further, in an embodiment, resource allocation within a processor, such as behavioral processing unit 500, may be based, at least in part, on behavioral profile content specification parameters, such as parameters 519. In an embodiment, a control unit, such as control unit 503, may obtain behavioral profile content specification parameters 519 that may indicate one or more behavioral profile parameters to be relatively prioritized, for example, and may select particular sensor processing units 505 and/or particular machine-learning units 506 based, at least in part, on the specified behavioral profile content parameters. "Relatively prioritized" in the context of behavioral profile content specification parameters, such as parameters 519, refers to one or more particular parameters to be processed on a priority basis over other parameters. For example, behavioral profile content specification parameters 519 may indicate an "anger" parameter. Resources (e.g., SPUs 505, machine-learning units 506, memory, etc.) sufficient to process the "anger" parameter to a particular confidence level, for example, may be allocated, even at the expense of resources that may otherwise be allocated to generating other behavioral profile content parameters. Control unit 503 may, via one or more control signals, select resources from sensor processing stage 501 and/or machine-learning stage 502 to generate behavioral profile content in accordance with the specified parameters. In this manner, relatively prioritized content may be generated relatively more efficiently. Behavioral profile content specification parameters, such as parameters 519, may also indicate relative priorities related to trade-offs between power consumption and generation of particular behavioral profile content, in an embodiment. Further, in an embodiment, relatively prioritized content may be generated at the relative expense of other behavioral profile content. For example, behavioral profile parameters indicating anger and/or fatigue may be relatively prioritized over excitement and/or hunger parameters, and control unit 503 may configure sensor processing stage 501 and/or machine-learning stage 502 accordingly. Further, in an embodiment, self-feedback and/or output monitoring content, such as content 520, may allow for control adjustments, such as selecting additional/different machine-learning units and/or sensor processing units and/or otherwise adjusting resource utilization within behavioral processing unit 500. Such adjustments may be made, for example, to meet specified relative priorities, specified levels of confidence in generated output, etc.

Although some embodiments described herein mention neural network techniques for machine learning, subject matter is not limited in scope in this respect. Other embodiments may incorporate other machine learning techniques either presently existing or to be developed in the future. Further, for embodiments implementing neural networks, for example, sensors may be removed from a system during offline pre-deployment training operations such that a neural network may determine appropriate weights for various sensor combinations. In another embodiment, during online operation, for example, a set of input biomarkers may be logged and/or later used as training parameters, wherein a predicted behavioral processing unit output may be utilized at least in part to train one or more networks that may lack some subset of the initial inputs. For online inference, an appropriate neural network may be selected based at least in part on available sensor inputs. Such an arrangement may be advantageous in situations wherein an operator may remove one or more sensors from a system, device, and/or process. For example, during surgery, a surgeon may remove his or her glasses that may have been tracking eye movement. In an embodiment, a different neural network configuration may be selected at least in part in response to such a change in available sensor input, for example. For example, a control unit, such as control unit 503, may detect a change in sensor availability (e.g., signified by sensor availability input 514), and/or may reconfigure sensor processing units 505 and/or machine-learning units 506 based at least in part on the detected change in sensor availability.

Figure 6:
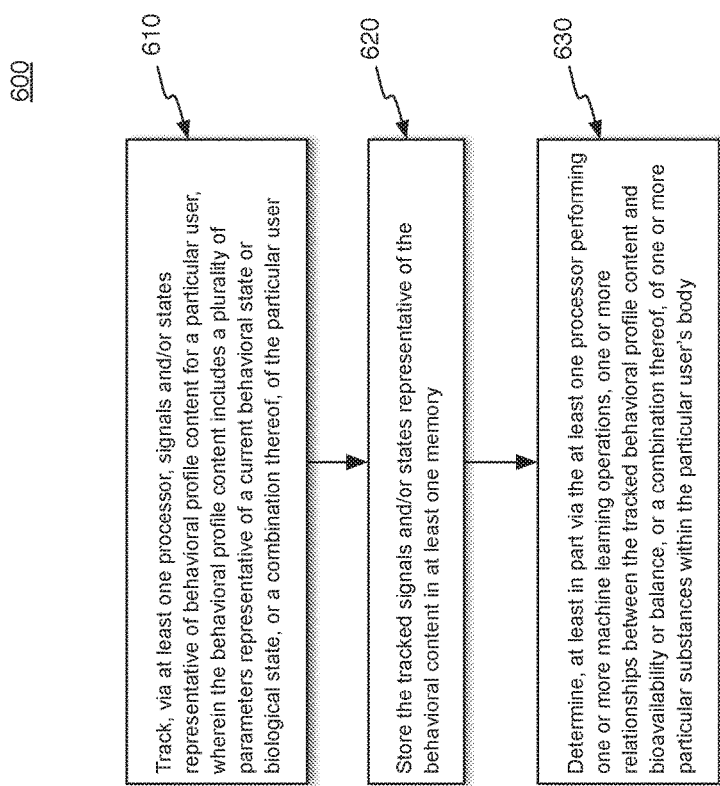
FIG. 6 is an illustration of an example process for tracking signals and/or states representative of behavioral profile content, in accordance with an embodiment.

FIG. 6 is an illustration of an embodiment 600 of an example process for tracking signals and/or states representative of behavioral profile content. Embodiments in accordance with claimed subject matter may include all of blocks 610-630, fewer than blocks 610-630, and/or more than blocks 610-630. Further, the order of blocks 610-630 is merely an example order, and claimed subject matter is not limited in scope in these respects.

As indicated at block 610, one or more signals and/or states representative of behavioral profile content for a particular user may be tracked via at least one processor of at least one computing device, wherein the behavioral profile content may include a plurality of parameters representative of a substantially current behavioral state or biological state, or a combination thereof, of the particular user. Further, as indicated at 620, signals and/or states representative of tracked behavioral profile content may be stored in at least one memory of a computing device.

Further, as indicated at block 630, one or more relationships between tracked behavioral profile content and a bioavailability and/or balance of one or more particular substances with a particular user's body. In an embodiment, recommendations for the particular user may be generated via at least one processor based at least in part on the behavioral profile content and/or based at least in part on one or more parameters representative of external factors, or a combination thereof, wherein the one or more recommendations may be substantially directed to improvement of a future state of the particular user.

In an embodiment, a decision-making device, system, and/or process, such as decision-making system 540, may determine, at least in part via at least one processor performing one or more machine learning operations, one or more relationships between tracked behavioral profile content, such as behavioral profile content 525 and bioavailability and/or balance, or a combination thereof, of one or more particular substances within a particular user's body. An embodiment may further include a decision-making device, system, and/or process, such as decision-making system 540, to generate one or more recommendations for supplementation related to particular one or more substances for a particular user, wherein one or more recommendations may be directed to improvement of a subsequent state of a particular user.

In the context of the present patent application, the term "connection," the term "component" and/or similar terms are intended to be physical, but are not necessarily always tangible. Whether or not these terms refer to tangible subject matter, thus, may vary in a particular context of usage. As an example, a tangible connection and/or tangible connection path may be made, such as by a tangible, electrical connection, such as an electrically conductive path comprising metal or other conductor, that is able to conduct electrical current between two tangible components. Likewise, a tangible connection path may be at least partially affected and/or controlled, such that, as is typical, a tangible connection path may be open or closed, at times resulting from influence of one or more externally derived signals, such as external currents and/or voltages, such as for an electrical switch. Non-limiting illustrations of an electrical switch include a transistor, a diode, etc. However, a "connection" and/or "component," in a particular context of usage, likewise, although physical, can also be non-tangible, such as a connection between a client and a server over a network, which generally refers to the ability for the client and server to transmit, receive, and/or exchange communications, as discussed in more detail later. Also, the term "connection" may be utilized in a context of a neural network model, and may, in an embodiment, refer to parameters passed between nodes that may include parameters and/or sets of parameters representative of output values, for example. Also, in an embodiment, connections between nodes may include weight parameters. For example, one or more weight parameters may operate in a specified manner on one or more parameters representative of one or more output values to yield a connection, such as between a node of a first layer and a node of a second layer, in an embodiment, for example.

In a particular context of usage, such as a particular context in which tangible components are being discussed, therefore, the terms "coupled" and "connected" are used in a manner so that the terms are not synonymous. Similar terms may also be used in a manner in which a similar intention is exhibited. Thus, "connected" is used to indicate that two or more tangible components and/or the like, for example, are tangibly in direct physical contact. Thus, using the previous example, two tangible components that are electrically connected are physically connected via a tangible electrical connection, as previously discussed. However, "coupled," is used to mean that potentially two or more tangible components are tangibly in direct physical contact. Nonetheless, is also used to mean that two or more tangible components and/or the like are not necessarily tangibly in direct physical contact, but are able to co-operate, liaise, and/or interact, such as, for example, by being "optically coupled." Likewise, the term "coupled" is also understood to mean indirectly connected. It is further noted, in the context of the present patent application, since memory, such as a memory component and/or memory states, is intended to be non-transitory, the term physical, at least if used in relation to memory necessarily implies that such memory components and/or memory states, continuing with the example, are tangible.

Additionally, in the present patent application, in a particular context of usage, such as a situation in which tangible components (and/or similarly, tangible materials) are being discussed, a distinction exists between being "on" and being "over." As an example, deposition of a substance "on" a substrate refers to a deposition involving direct physical and tangible contact without an intermediary, such as an intermediary substance, between the substance deposited and the substrate in this latter example; nonetheless, deposition "over" a substrate, while understood to potentially include deposition "on" a substrate (since being "on" may also accurately be described as being "over"), is understood to include a situation in which one or more intermediaries, such as one or more intermediary substances, are present between the substance deposited and the substrate so that the substance deposited is not necessarily in direct physical and tangible contact with the substrate.

A similar distinction is made in an appropriate particular context of usage, such as in which tangible materials and/or tangible components are discussed, between being "beneath" and being "under." While "beneath," in such a particular context of usage, is intended to necessarily imply physical and tangible contact (similar to "on," as just described), "under" potentially includes a situation in which there is direct physical and tangible contact, but does not necessarily imply direct physical and tangible contact, such as if one or more intermediaries, such as one or more intermediary substances, are present. Thus, "on" is understood to mean "immediately over" and "beneath" is understood to mean "immediately under."

It is likewise appreciated that terms such as "over" and "under" are understood in a similar manner as the terms "up," "down," "top," "bottom," and so on, previously mentioned. These terms may be used to facilitate discussion, but are not intended to necessarily restrict scope of claimed subject matter. For example, the term "over," as an example, is not meant to suggest that claim scope is limited to only situations in which an embodiment is right side up, such as in comparison with the embodiment being upside down, for example. An example includes a flip chip, as one illustration, in which, for example, orientation at various times (e.g., during fabrication) may not necessarily correspond to orientation of a final product. Thus, if an object, as an example, is within applicable claim scope in a particular orientation, such as upside down, as one example, likewise, it is intended that the latter also be interpreted to be included within applicable claim scope in another orientation, such as right side up, again, as an example, and vice-versa, even if applicable literal claim language has the potential to be interpreted otherwise. Of course, again, as always has been the case in the specification of a patent application, particular context of description and/or usage provides helpful guidance regarding reasonable inferences to be drawn.

Unless otherwise indicated, in the context of the present patent application, the term "or" if used to associate a list, such as A, B, or C, is intended to mean A, B, and C, here used in the inclusive sense, as well as A, B, or C, here used in the exclusive sense. With this understanding, "and" is used in the inclusive sense and intended to mean A, B, and C; whereas "and/or" can be used in an abundance of caution to make clear that all of the foregoing meanings are intended, although such usage is not required. In addition, the term "one or more" and/or similar terms is used to describe any feature, structure, characteristic, and/or the like in the singular, "and/or" is also used to describe a plurality and/or some other combination of features, structures, characteristics, and/or the like. Likewise, the term "based on" and/or similar terms are understood as not necessarily intending to convey an exhaustive list of factors, but to allow for existence of additional factors not necessarily expressly described.

Furthermore, it is intended, for a situation that relates to implementation of claimed subject matter and is subject to testing, measurement, and/or specification regarding degree, to be understood in the following manner. As an example, in a given situation, assume a value of a physical property is to be measured. If alternatively reasonable approaches to testing, measurement, and/or specification regarding degree, at least with respect to the property, continuing with the example, is reasonably likely to occur to one of ordinary skill, at least for implementation purposes, claimed subject matter is intended to cover those alternatively reasonable approaches unless otherwise expressly indicated. As an example, if a plot of measurements over a region is produced and implementation of claimed subject matter refers to employing a measurement of slope over the region, but a variety of reasonable and alternative techniques to estimate the slope over that region exist, claimed subject matter is intended to cover those reasonable alternative techniques unless otherwise expressly indicated.

To the extent claimed subject matter is related to one or more particular measurements, such as with regard to physical manifestations capable of being measured physically, such as, without limit, temperature, pressure, voltage, current, electromagnetic radiation, etc., it is believed that claimed subject matter does not fall with the abstract idea judicial exception to statutory subject matter. Rather, it is asserted, that physical measurements are not mental steps and, likewise, are not abstract ideas.

It is noted, nonetheless, that a typical measurement model employed is that one or more measurements may respectively comprise a sum of at least two components. Thus, for a given measurement, for example, one component may comprise a deterministic component, which in an ideal sense, may comprise a physical value (e.g., sought via one or more measurements), often in the form of one or more signals, signal samples and/or states, and one component may comprise a random component, which may have a variety of sources that may be challenging to quantify. At times, for example, lack of measurement precision may affect a given measurement. Thus, for claimed subject matter, a statistical or stochastic model may be used in addition to a deterministic model as an approach to identification and/or prediction regarding one or more measurement values that may relate to claimed subject matter.

For example, a relatively large number of measurements may be collected to better estimate a deterministic component. Likewise, if measurements vary, which may typically occur, it may be that some portion of a variance may be explained as a deterministic component, while some portion of a variance may be explained as a random component. Typically, it is desirable to have stochastic variance associated with measurements be relatively small, if feasible. That is, typically, it may be preferable to be able to account for a reasonable portion of measurement variation in a deterministic manner, rather than a stochastic matter as an aid to identification and/or predictability.

Along these lines, a variety of techniques have come into use so that one or more measurements may be processed to better estimate an underlying deterministic component, as well as to estimate potentially random components. These techniques, of course, may vary with details surrounding a given situation. Typically, however, more complex problems may involve use of more complex techniques. In this regard, as alluded to above, one or more measurements of physical manifestations may be modeled deterministically and/or stochastically. Employing a model permits collected measurements to potentially be identified and/or processed, and/or potentially permits estimation and/or prediction of an underlying deterministic component, for example, with respect to later measurements to be taken. A given estimate may not be a perfect estimate; however, in general, it is expected that on average one or more estimates may better reflect an underlying deterministic component, for example, if random components that may be included in one or more obtained measurements, are considered. Practically speaking, of course, it is desirable to be able to generate, such as through estimation approaches, a physically meaningful model of processes affecting measurements to be taken.

In some situations, however, as indicated, potential influences may be complex. Therefore, seeking to understand appropriate factors to consider may be particularly challenging. In such situations, it is, therefore, not unusual to employ heuristics with respect to generating one or more estimates. Heuristics refers to use of experience related approaches that may reflect realized processes and/or realized results, such as with respect to use of historical measurements, for example. Heuristics, for example, may be employed in situations where more analytical approaches may be overly complex and/or nearly intractable. Thus, regarding claimed subject matter, an innovative feature may include, in an example embodiment, heuristics that may be employed, for example, to estimate and/or predict one or more measurements.

It is further noted that the terms "type" and/or "like," if used, such as with a feature, structure, characteristic, and/or the like, using "optical" or "electrical" as simple examples, means at least partially of and/or relating to the feature, structure, characteristic, and/or the like in such a way that presence of minor variations, even variations that might otherwise not be considered fully consistent with the feature, structure, characteristic, and/or the like, do not in general prevent the feature, structure, characteristic, and/or the like from being of a "type" and/or being "like," (such as being an "optical-type" or being "optical-like," for example) if the minor variations are sufficiently minor so that the feature, structure, characteristic, and/or the like would still be considered to be substantially present with such variations also present. Thus, continuing with this example, the terms optical-type and/or optical-like properties are necessarily intended to include optical properties. Likewise, the terms electrical-type and/or electrical-like properties, as another example, are necessarily intended to include electrical properties. It should be noted that the specification of the present patent application merely provides one or more illustrative examples and claimed subject matter is intended to not be limited to one or more illustrative examples; however, again, as has always been the case with respect to the specification of a patent application, particular context of description and/or usage provides helpful guidance regarding reasonable inferences to be drawn.

In the context of the present patent application, the term network device refers to any device capable of communicating via and/or as part of a network and may comprise a computing device. While network devices may be capable of communicating signals (e.g., signal packets and/or frames), such as via a wired and/or wireless network, they may also be capable of performing operations associated with a computing device, such as arithmetic and/or logic operations, processing and/or storing operations (e.g., storing signal samples), such as in memory as tangible, physical memory states, and/or may, for example, operate as a server device and/or a client device in various embodiments. Network devices capable of operating as a server device, a client device and/or otherwise, may include, as examples, dedicated rack-mounted servers, desktop computers, laptop computers, set top boxes, tablets, netbooks, smart phones, wearable devices, integrated devices combining two or more features of the foregoing devices, and/or the like, or any combination thereof. As mentioned, signal packets and/or frames, for example, may be exchanged, such as between a server device and/or a client device, as well as other types of devices, including between wired and/or wireless devices coupled via a wired and/or wireless network, for example, or any combination thereof. It is noted that the terms, server, server device, server computing device, server computing platform and/or similar terms are used interchangeably. Similarly, the terms client, client device, client computing device, client computing platform and/or similar terms are also used interchangeably. While in some instances, for ease of description, these terms may be used in the singular, such as by referring to a "client device" or a "server device," the description is intended to encompass one or more client devices and/or one or more server devices, as appropriate. Along similar lines, references to a "database" are understood to mean, one or more databases and/or portions thereof, as appropriate.

It should be understood that for ease of description, a network device (also referred to as a networking device) may be embodied and/or described in terms of a computing device and vice-versa. However, it should further be understood that this description should in no way be construed so that claimed subject matter is limited to one embodiment, such as only a computing device and/or only a network device, but, instead, may be embodied as a variety of devices or combinations thereof, including, for example, one or more illustrative examples.

A network may also include now known, and/or to be later developed arrangements, derivatives, and/or improvements, including, for example, past, present and/or future mass storage, such as network attached storage (NAS), a storage area network (SAN), and/or other forms of device readable media, for example. A network may include a portion of the Internet, one or more local area networks (LANs), one or more wide area networks (WANs), wire-line type connections, wireless type connections, other connections, or any combination thereof. Thus, a network may be worldwide in scope and/or extent. Likewise, sub-networks, such as may employ differing architectures and/or may be substantially compliant and/or substantially compatible with differing protocols, such as network computing and/or communications protocols (e.g., network protocols), may interoperate within a larger network.

The term electronic file and/or the term electronic document are used throughout this document to refer to a set of stored memory states and/or a set of physical signals associated in a manner so as to thereby at least logically form a file (e.g., electronic) and/or an electronic document. That is, it is not meant to implicitly reference a particular syntax, format and/or approach used, for example, with respect to a set of associated memory states and/or a set of associated physical signals. If a particular type of file storage format and/or syntax, for example, is intended, it is referenced expressly. It is further noted an association of memory states, for example, may be in a logical sense and not necessarily in a tangible, physical sense. Thus, although signal and/or state components of a file and/or an electronic document, for example, are to be associated logically, storage thereof, for example, may reside in one or more different places in a tangible, physical memory, in an embodiment.

In the context of the present patent application, the terms "entry," "electronic entry," "document," "electronic document," "content,", "digital content," "item," and/or similar terms are meant to refer to signals and/or states in a physical format, such as a digital signal and/or digital state format, e.g., that may be perceived by a user if displayed, played, tactilely generated, etc. and/or otherwise executed by a device, such as a digital device, including, for example, a computing device, but otherwise might not necessarily be readily perceivable by humans (e.g., if in a digital format). Likewise, in the context of the present patent application, digital content provided to a user in a form so that the user is able to readily perceive the underlying content itself (e.g., content presented in a form consumable by a human, such as hearing audio, feeling tactile sensations and/or seeing images, as examples) is referred to, with respect to the user, as "consuming" digital content, "consumption" of digital content, "consumable" digital content and/or similar terms. For one or more embodiments, an electronic document and/or an electronic file may comprise a Web page of code (e.g., computer instructions) in a markup language executed or to be executed by a computing and/or networking device, for example. In another embodiment, an electronic document and/or electronic file may comprise a portion and/or a region of a Web page. However, claimed subject matter is not intended to be limited in these respects.

Also, for one or more embodiments, an electronic document and/or electronic file may comprise a number of components. As previously indicated, in the context of the present patent application, a component is physical, but is not necessarily tangible. As an example, components with reference to an electronic document and/or electronic file, in one or more embodiments, may comprise text, for example, in the form of physical signals and/or physical states (e.g., capable of being physically displayed). Typically, memory states, for example, comprise tangible components, whereas physical signals are not necessarily tangible, although signals may become (e.g., be made) tangible, such as if appearing on a tangible display, for example, as is not uncommon. Also, for one or more embodiments, components with reference to an electronic document and/or electronic file may comprise a graphical object, such as, for example, an image, such as a digital image, and/or sub-objects, including attributes thereof, which, again, comprise physical signals and/or physical states (e.g., capable of being tangibly displayed). In an embodiment, digital content may comprise, for example, text, images, audio, video, and/or other types of electronic documents and/or electronic files, including portions thereof, for example.

Also, in the context of the present patent application, the term parameters (e.g., one or more parameters) refer to material descriptive of a collection of signal samples, such as one or more electronic documents and/or electronic files, and exist in the form of physical signals and/or physical states, such as memory states. For example, one or more parameters, such as referring to an electronic document and/or an electronic file comprising an image, may include, as examples, time of day at which an image was captured, latitude and longitude of an image capture device, such as a camera, for example, etc. In another example, one or more parameters relevant to digital content, such as digital content comprising a technical article, as an example, may include one or more authors, for example. Claimed subject matter is intended to embrace meaningful, descriptive parameters in any format, so long as the one or more parameters comprise physical signals and/or states, which may include, as parameter examples, collection name (e.g., electronic file and/or electronic document identifier name), technique of creation, purpose of creation, time and date of creation, logical path if stored, coding formats (e.g., type of computer instructions, such as a markup language) and/or standards and/or specifications used so as to be protocol compliant (e.g., meaning substantially compliant and/or substantially compatible) for one or more uses, and so forth.

Signal packet communications and/or signal frame communications, also referred to as signal packet transmissions and/or signal frame transmissions (or merely "signal packets" or "signal frames"), may be communicated between nodes of a network, where a node may comprise one or more network devices and/or one or more computing devices, for example. As an illustrative example, but without limitation, a node may comprise one or more sites employing a local network address, such as in a local network address space. Likewise, a device, such as a network device and/or a computing device, may be associated with that node. It is also noted that in the context of this patent application, the term "transmission" is intended as another term for a type of signal communication that may occur in any one of a variety of situations. Thus, it is not intended to imply a particular directionality of communication and/or a particular initiating end of a communication path for the "transmission" communication. For example, the mere use of the term in and of itself is not intended, in the context of the present patent application, to have particular implications with respect to the one or more signals being communicated, such as, for example, whether the signals are being communicated "to" a particular device, whether the signals are being communicated "from" a particular device, and/or regarding which end of a communication path may be initiating communication, such as, for example, in a "push type" of signal transfer or in a "pull type" of signal transfer. In the context of the present patent application, push and/or pull type signal transfers are distinguished by which end of a communications path initiates signal transfer.

Thus, a signal packet and/or frame may, as an example, be communicated via a communication channel and/or a communication path, such as comprising a portion of the Internet and/or the Web, from a site via an access node coupled to the Internet or vice-versa. Likewise, a signal packet and/or frame may be forwarded via network nodes to a target site coupled to a local network, for example. A signal packet and/or frame communicated via the Internet and/or the Web, for example, may be routed via a path, such as either being "pushed" or "pulled," comprising one or more gateways, servers, etc. that may, for example, route a signal packet and/or frame, such as, for example, substantially in accordance with a target and/or destination address and availability of a network path of network nodes to the target and/or destination address. Although the Internet and/or the Web comprise a network of interoperable networks, not all of those interoperable networks are necessarily available and/or accessible to the public.

In the context of the particular patent application, a network protocol, such as for communicating between devices of a network, may be characterized, at least in part, substantially in accordance with a layered description, such as the so-called Open Systems Interconnection (OSI) seven layer type of approach and/or description. A network computing and/or communications protocol (also referred to as a network protocol) refers to a set of signaling conventions, such as for communication transmissions, for example, as may take place between and/or among devices in a network. In the context of the present patent application, the term "between" and/or similar terms are understood to include "among" if appropriate for the particular usage and vice-versa. Likewise, in the context of the present patent application, the terms "compatible with," "comply with" and/or similar terms are understood to respectively include substantial compatibility and/or substantial compliance.

A network protocol, such as protocols characterized substantially in accordance with the aforementioned OSI description, has several layers. These layers are referred to as a network stack. Various types of communications (e.g., transmissions), such as network communications, may occur across various layers. A lowest level layer in a network stack, such as the so-called physical layer, may characterize how symbols (e.g., bits and/or bytes) are communicated as one or more signals (and/or signal samples) via a physical medium (e.g., twisted pair copper wire, coaxial cable, fiber optic cable, wireless air interface, combinations thereof, etc.). Progressing to higher-level layers in a network protocol stack, additional operations and/or features may be available via engaging in communications that are substantially compatible and/or substantially compliant with a particular network protocol at these higher-level layers. For example, higher-level layers of a network protocol may, for example, affect device permissions, user permissions, etc.

A network and/or sub-network, in an embodiment, may communicate via signal packets and/or signal frames, such via participating digital devices and may be substantially compliant and/or substantially compatible with, but is not limited to, now known and/or to be developed, versions of any of the following network protocol stacks: ARCNET, AppleTalk, ATM, Bluetooth, DECnet, Ethernet, FDDI, Frame Relay, HIPPI, IEEE 1394, IEEE 802.11, IEEE-488, Internet Protocol Suite, IPX, Myrinet, OSI Protocol Suite, QsNet, RS-232, SPX, System Network Architecture, Token Ring, USB, and/or X.25. A network and/or sub-network may employ, for example, a version, now known and/or later to be developed, of the following: TCP/IP, UDP, DECnet, NetBEUI, IPX, AppleTalk and/or the like. Versions of the Internet Protocol (IP) may include IPv4, IPv6, and/or other later to be developed versions.

Regarding aspects related to a network, including a communications and/or computing network, a wireless network may couple devices, including client devices, with the network. A wireless network may employ stand-alone, ad-hoc networks, mesh networks, Wireless LAN (WLAN) networks, cellular networks, and/or the like. A wireless network may further include a system of terminals, gateways, routers, and/or the like coupled by wireless radio links, and/or the like, which may move freely, randomly and/or organize themselves arbitrarily, such that network topology may change, at times even rapidly. A wireless network may further employ a plurality of network access technologies, including a version of Long Term Evolution (LTE), WLAN, Wireless Router (WR) mesh, 2nd, 3rd, or 4th generation (2G, 3G, or 4G) cellular technology and/or the like, whether currently known and/or to be later developed. Network access technologies may enable wide area coverage for devices, such as computing devices and/or network devices, with varying degrees of mobility, for example.

A network may enable radio frequency and/or other wireless type communications via a wireless network access technology and/or air interface, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, ultra-wideband (UWB), 802.11b/g/n, and/or the like. A wireless network may include virtually any type of now known and/or to be developed wireless communication mechanism and/or wireless communications protocol by which signals may be communicated between devices, between networks, within a network, and/or the like, including the foregoing, of course.

Figure 7:
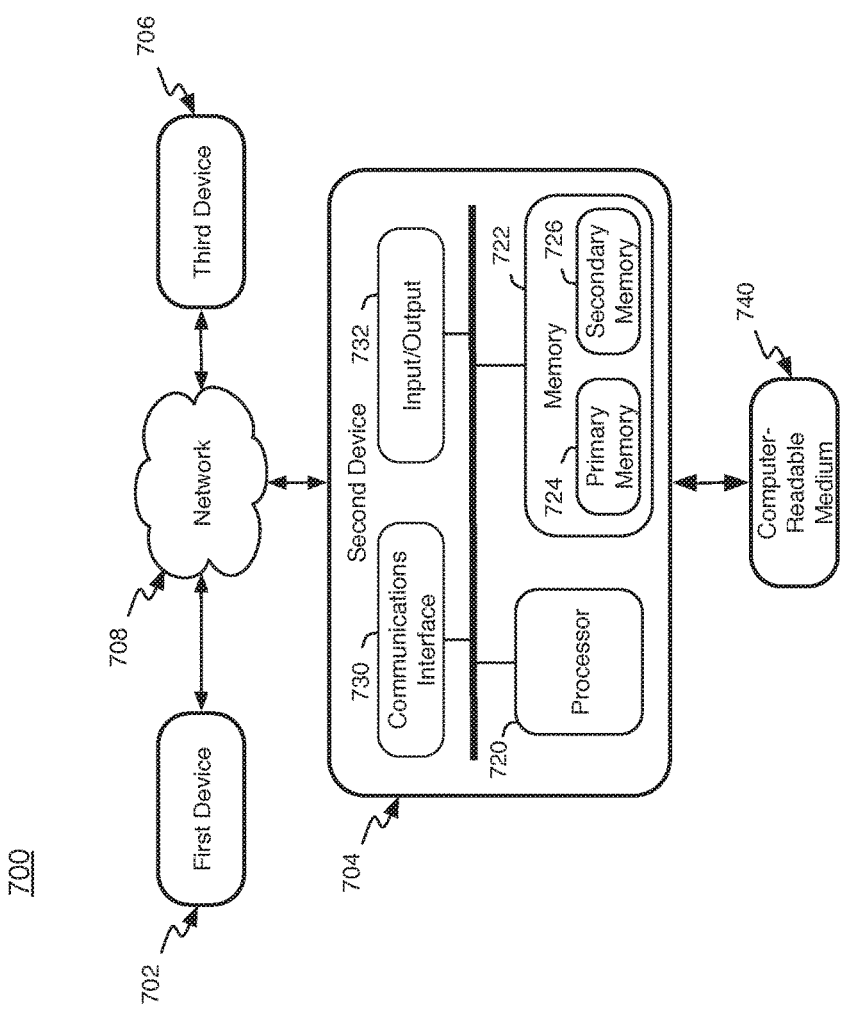
FIG. 7 is a schematic block diagram of an example computing device, in accordance with an embodiment.

In one example embodiment, as shown in FIG. 7, a system embodiment may comprise a local network (e.g., device 704 and medium 740) and/or another type of network, such as a computing and/or communications network. For purposes of illustration, therefore, FIG. 7 shows an embodiment 700 of a system that may be employed to implement either type or both types of networks. Network 708 may comprise one or more network connections, links, processes, services, applications, and/or resources to facilitate and/or support communications, such as an exchange of communication signals, for example, between a computing device, such as 702, and another computing device, such as 706, which may, for example, comprise one or more client computing devices and/or one or more server computing device. By way of example, but not limitation, network 708 may comprise wireless and/or wired communication links, telephone and/or telecommunications systems, Wi-Fi networks, Wi-MAX networks, the Internet, a local area network (LAN), a wide area network (WAN), or any combinations thereof.

Example devices in FIG. 7 may comprise features, for example, of a client computing device and/or a server computing device, in an embodiment. It is further noted that the term computing device, in general, whether employed as a client and/or as a server, or otherwise, refers at least to a processor and a memory connected by a communication bus. Likewise, in the context of the present patent application at least, this is understood to refer to sufficient structure within the meaning of 35 USC § 112 (f) so that it is specifically intended that 35 USC § 112 (f) not be implicated by use of the term "computing device" and/or similar terms; however, if it is determined, for some reason not immediately apparent, that the foregoing understanding cannot stand and that 35 USC § 112 (f), therefore, necessarily is implicated by the use of the term "computing device" and/or similar terms, then, it is intended, pursuant to that statutory section, that corresponding structure, material and/or acts for performing one or more functions be understood and be interpreted to be described at least in FIGS. 1-6, for example, and in the text associated with the foregoing figure(s) of the present patent application.

An embodiment in accordance with claimed subject matter may include a method of executing computer instructions on at least one computing device without further human interaction in which the at least one computing device includes at least one processor and at least one memory. An embodiment may include fetching computer instructions from the at least one memory of the at least one computing device for execution on the at least one processor of the at least one computing device, executing the fetched computer instructions on the at least one processor of the at least one computing device, and storing in the at least one memory of the at least one computing device any results of having executed the fetched computer instructions on the at least one processor of the at least one computing device. In an embodiment, the computer instructions to be executed comprise instructions for processing content representative of a behavioral and/or biological state of a particular user, wherein executing the fetched instructions further includes tracking, via at least one processor, signals and/or states representative of behavioral profile content for a particular user, wherein the behavioral profile content includes a plurality of parameters representative of a current behavioral state or biological state, or a combination thereof, of the particular user, storing the tracked signals and/or states representative of the behavioral content in at least one memory, and determining, at least in part via the at least one processor performing one or more machine learning operations, one or more relationships between the tracked behavioral profile content and bioavailability or balance, or a combination thereof, of one or more particular substances within the particular user's body.

An embodiment may further include generating, at least in part via the at least one processor, one or more recommendations for supplementation related to the particular one or more substances for the particular user, wherein the one or more recommendations are directed to improvement of a subsequent state of the particular user. In an embodiment, generating the one or more recommendations may include generating the one or more recommendations based at least in part on current behavioral profile content for the particular user or based at least in part on the one or more determined relationships, or a combination thereof.

In an embodiment, behavioral profile content may include one or more parameters representative of eye movement for the particular user. Further, performing one or more machine learning operations may include performing one or more training operations based at least in part on input obtained from one or more users. Input obtained from one or more users may include content representative of intake by the particular user of supplementation related to the particular one or more substances. Additionally, input obtained from the one or more users may further include content representative of one or more aspects of one or more scientific publications directed, at least in part, to the particular one or more substances. In an embodiment, the one or more particular substances within the particular user's body may include gamma-aminobutyric acid (GABA) or glutamate, or a combination thereof.

Further, in an embodiment, determining one or more relationships between tracked behavioral profile content and bioavailability or balance, or a combination thereof, of one or more particular substances within a particular user's body may include determining one or more relationships between one or more parameters representative of eye movement and a balance between the GABA and the glutamate within the particular user's body. In an embodiment, one or more particular substances within the particular user's body may include 5-methyltetrahydrofolate. Additionally, in an embodiment, determining one or more relationships between tracked behavioral profile content and the bioavailability or balance, or a combination thereof, of the one or more particular substances within the particular user's body may include determining one or more relationships between the one or more parameters representative of the eye movement and a bioavailability of the 5-methyltetrahydrofolate within the particular user's body.

In an embodiment, an apparatus may include at least one computing device, the at least one computing device including at least one processor and at least one memory, the at least one computing device to execute computer instructions on the at least one processor without further human intervention. In an embodiment, the computer instructions to be executed may be fetched from the at least one memory for execution on the at least one processor, and the at least one computing device may store in the at least one memory of the at least one computing device any results to be generated from the execution on the at least one processor of the to be executed computer instructions. In an embodiment, the computer instructions to be executed may include instructions to process content representative of a behavioral and/or biological state of a particular user. In an embodiment, the at least one processor may track signals and/or states representative of behavioral profile content for a particular user, the behavioral profile content to include a plurality of parameters representative of a current behavioral state or biological state, or a combination thereof, of the particular user, the at least one memory to store the tracked signals and/or states representative of the behavioral content, wherein the at least one processor to perform one or more machine learning operations to determine one or more relationships between the tracked behavioral profile content and bioavailability or balance, or a combination thereof, of one or more particular substances within the particular user's body.

Additionally, in an embodiment, the at least one processor further to generate one or more recommendations for supplementation related to the particular one or more substances for the particular user, the one or more recommendations to be directed to improvement of a subsequent state of the particular user. Further, the at least one processor to generate the one or more recommendations to be based at least in part on current behavioral profile content for the particular user or to be based at least in part on the one or more determined relationships, or a combination thereof. The behavioral profile content to comprise one or more parameters representative of eye movement for the particular user, in an embodiment.

Further, in an embodiment, to perform the one or more machine learning operations, the at least one processor to perform one or more training operations to be based at least in part on input to be obtained from one or more users. In an embodiment, input to be obtained from one or more users may include content representative of intake by the particular user of supplementation related to the particular one or more substances. Additionally, the input to be obtained from the one or more users may further include content representative of one or more aspects of one or more scientific publications directed, at least in part, to the particular one or more substances. The one or more particular substances within the particular user's body may include gamma-aminobutyric acid (GABA) or glutamate, or a combination thereof, for example.

In an embodiment, the at least one processor may perform one or more machine learning operations to determine the one or more relationships between the one or more parameters representative of the eye movement and a balance between the GABA and the glutamate within the particular user's body. Further, in an embodiment, the one or more particular substances within the particular user's body may include 5-methyltetrahydrofolate. In an embodiment, at least one processor may perform one or more machine learning operations to determine one or more relationships between one or more parameters representative of the eye movement and a bioavailability of the 5-methyltetrahydrofolate within the particular user's body.

Referring now again to FIG. 7, in an embodiment, first and third devices 702 and 706 may be capable of rendering a graphical user interface (GUI) for a network device and/or a computing device, for example, so that a user-operator may engage in system use. Device 704 may potentially serve a similar function in this illustration. Likewise, in FIG. 7, computing device 702 ('first device' in figure) may interface with computing device 704 ('second device' in figure), which may, for example, also comprise features of a client computing device and/or a server computing device, in an embodiment. Processor (e.g., processing device) 720 and memory 722, which may comprise primary memory 724 and secondary memory 726, may communicate by way of a communication bus 715, for example. The term "computing device," in the context of the present patent application, refers to a system and/or a device, such as a computing apparatus, that includes a capability to process (e.g., perform computations) and/or store digital content, such as electronic files, electronic documents, parameters, measurements, text, images, video, audio, etc. in the form of signals and/or states. Thus, a computing device, in the context of the present patent application, may comprise hardware, software, firmware, or any combination thereof (other than software per se). Computing device 704, as depicted in FIG. 7, is merely one example, and claimed subject matter is not limited in scope to this particular example.

As mentioned, for one or more embodiments, a computing device may comprise, for example, any of a wide range of digital electronic devices, including, but not limited to, desktop and/or notebook computers, high-definition televisions, digital versatile disc (DVD) and/or other optical disc players and/or recorders, game consoles, satellite television receivers, cellular telephones, tablet devices, wearable devices, personal digital assistants, mobile audio and/or video playback and/or recording devices, or any combination of the foregoing. Further, unless specifically stated otherwise, a process as described, such as with reference to flow diagrams and/or otherwise, may also be executed and/or affected, in whole or in part, by a computing device and/or a network device. A device, such as a computing device and/or network device, may vary in terms of capabilities and/or features. Claimed subject matter is intended to cover a wide range of potential variations. For example, a device may include a numeric keypad and/or other display of limited functionality, such as a monochrome liquid crystal display (LCD) for displaying text, for example. In contrast, however, as another example, a web-enabled device may include a physical and/or a virtual keyboard, mass storage, one or more accelerometers, one or more gyroscopes, global positioning system (GPS) and/or other location-identifying type capability, and/or a display with a higher degree of functionality, such as a touch-sensitive color 2D or 3D display, for example.

As suggested previously, communications between a computing device and/or a network device and a wireless network may be in accordance with known and/or to be developed network protocols including, for example, global system for mobile communications (GSM), enhanced data rate for GSM evolution (EDGE), 802.11b/g/n/h, etc., and/or worldwide interoperability for microwave access (Wi-MAX). A computing device and/or a networking device may also have a subscriber identity module (SIM) card, which, for example, may comprise a detachable or embedded smart card that is able to store subscription content of a user, and/or is also able to store a contact list. A user may own the computing device and/or network device or may otherwise be a user, such as a primary user, for example. A device may be assigned an address by a wireless network operator, a wired network operator, and/or an Internet Service Provider (ISP). For example, an address may comprise a domestic or international telephone number, an Internet Protocol (IP) address, and/or one or more other identifiers. In other embodiments, a computing and/or communications network may be embodied as a wired network, wireless network, or any combinations thereof.

A computing and/or network device may include and/or may execute a variety of now known and/or to be developed operating systems, derivatives and/or versions thereof, including computer operating systems, such as Windows, iOS, Linux, a mobile operating system, such as iOS, Android, Windows Mobile, and/or the like. A computing device and/or network device may include and/or may execute a variety of possible applications, such as a client software application enabling communication with other devices. For example, one or more messages (e.g., content) may be communicated, such as via one or more protocols, now known and/or later to be developed, suitable for communication of email, short message service (SMS), and/or multimedia message service (MMS), including via a network, such as a social network, formed at least in part by a portion of a computing and/or communications network, including, but not limited to, Facebook, LinkedIn, Twitter, Flickr, and/or Google+, to provide only a few examples. A computing and/or network device may also include executable computer instructions to process and/or communicate digital content, such as, for example, textual content, digital multimedia content, and/or the like. A computing and/or network device may also include executable computer instructions to perform a variety of possible tasks, such as browsing, searching, playing various forms of digital content, including locally stored and/or streamed video, and/or games such as, but not limited to, fantasy sports leagues. The foregoing is provided merely to illustrate that claimed subject matter is intended to include a wide range of possible features and/or capabilities.

In FIG. 7, computing device 702 may provide one or more sources of executable computer instructions in the form physical states and/or signals (e.g., stored in memory states), for example. Computing device 702 may communicate with computing device 704 by way of a network connection, such as via network 708, for example. As previously mentioned, a connection, while physical, may not necessarily be tangible. Although computing device 704 of FIG. 7 shows various tangible, physical components, claimed subject matter is not limited to a computing devices having only these tangible components as other implementations and/or embodiments may include alternative arrangements that may comprise additional tangible components or fewer tangible components, for example, that function differently while achieving similar results. Rather, examples are provided merely as illustrations. It is not intended that claimed subject matter be limited in scope to illustrative examples.

Memory 722 may comprise any non-transitory storage mechanism. Memory 722 may comprise, for example, primary memory 724 and secondary memory 726, additional memory circuits, mechanisms, or combinations thereof may be used. Memory 722 may comprise, for example, random access memory, read only memory, etc., such as in the form of one or more storage devices and/or systems, such as, for example, a disk drive including an optical disc drive, a tape drive, a solid-state memory drive, etc., just to name a few examples.

Memory 722 may be utilized to store a program of executable computer instructions. For example, processor 720 may fetch executable instructions from memory and proceed to execute the fetched instructions. Memory 722 may also comprise a memory controller for accessing device readable-medium 740 that may carry and/or make accessible digital content, which may include code, and/or instructions, for example, executable by processor 720 and/or some other device, such as a controller, as one example, capable of executing computer instructions, for example. Under direction of processor 720, a non-transitory memory, such as memory cells storing physical states (e.g., memory states), comprising, for example, a program of executable computer instructions, may be executed by processor 720 and able to generate signals to be communicated via a network, for example, as previously described. Generated signals may also be stored in memory, also previously suggested.

Memory 722 may store electronic files and/or electronic documents, such as relating to one or more users, and may also comprise a computer-readable medium that may carry and/or make accessible content, including code and/or instructions, for example, executable by processor 720 and/or some other device, such as a controller, as one example, capable of executing computer instructions, for example. As previously mentioned, the term electronic file and/or the term electronic document are used throughout this document to refer to a set of stored memory states and/or a set of physical signals associated in a manner so as to thereby form an electronic file and/or an electronic document. That is, it is not meant to implicitly reference a particular syntax, format and/or approach used, for example, with respect to a set of associated memory states and/or a set of associated physical signals. It is further noted an association of memory states, for example, may be in a logical sense and not necessarily in a tangible, physical sense. Thus, although signal and/or state components of an electronic file and/or electronic document, are to be associated logically, storage thereof, for example, may reside in one or more different places in a tangible, physical memory, in an embodiment.

Algorithmic descriptions and/or symbolic representations are examples of techniques used by those of ordinary skill in the signal processing and/or related arts to convey the substance of their work to others skilled in the art. An algorithm is, in the context of the present patent application, and generally, is considered to be a self-consistent sequence of operations and/or similar signal processing leading to a desired result. In the context of the present patent application, operations and/or processing involve physical manipulation of physical quantities. Typically, although not necessarily, such quantities may take the form of electrical and/or magnetic signals and/or states capable of being stored, transferred, combined, compared, processed and/or otherwise manipulated, for example, as electronic signals and/or states making up components of various forms of digital content, such as signal measurements, text, images, video, audio, etc.

It has proven convenient at times, principally for reasons of common usage, to refer to such physical signals and/or physical states as bits, values, elements, parameters, symbols, characters, terms, numbers, numerals, measurements, content and/or the like. It should be understood, however, that all of these and/or similar terms are to be associated with appropriate physical quantities and are merely convenient labels. Unless specifically stated otherwise, as apparent from the preceding discussion, it is appreciated that throughout this specification discussions utilizing terms such as "processing," "computing," "calculating," "determining", "establishing", "obtaining", "identifying", "selecting", "generating", and/or the like may refer to actions and/or processes of a specific apparatus, such as a special purpose computer and/or a similar special purpose computing and/or network device. In the context of this specification, therefore, a special purpose computer and/or a similar special purpose computing and/or network device is capable of processing, manipulating and/or transforming signals and/or states, typically in the form of physical electronic and/or magnetic quantities, within memories, registers, and/or other storage devices, processing devices, and/or display devices of the special purpose computer and/or similar special purpose computing and/or network device. In the context of this particular patent application, as mentioned, the term "specific apparatus" therefore includes a general purpose computing and/or network device, such as a general purpose computer, once it is programmed to perform particular functions, such as pursuant to program software instructions.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and/or storage of charge or a release of stored charge. Likewise, in other memory devices, a change of state may comprise a physical change, such as a transformation in magnetic orientation. Likewise, a physical change may comprise a transformation in molecular structure, such as from crystalline form to amorphous form or vice-versa. In still other memory devices, a change in physical state may involve quantum mechanical phenomena, such as, superposition, entanglement, and/or the like, which may involve quantum bits (qubits), for example. The foregoing is not intended to be an exhaustive list of all examples in which a change in state from a binary one to a binary zero or vice-versa in a memory device may comprise a transformation, such as a physical, but non-transitory, transformation. Rather, the foregoing is intended as illustrative examples.

Referring again to FIG. 7, processor 720 may comprise one or more circuits, such as digital circuits, to perform at least a portion of a computing procedure and/or process. By way of example, but not limitation, processor 720 may comprise one or more processors, such as controllers, microprocessors, microcontrollers, application specific integrated circuits, digital signal processors, programmable logic devices, field programmable gate arrays, the like, or any combination thereof. In various implementations and/or embodiments, processor 720 may perform signal processing, typically substantially in accordance with fetched executable computer instructions, such as to manipulate signals and/or states, to construct signals and/or states, etc., with signals and/or states generated in such a manner to be communicated and/or stored in memory, for example.

FIG. 7 also illustrates device 704 as including a component 732 operable with input/output devices, for example, so that signals and/or states may be appropriately communicated between devices, such as device 704 and an input device and/or device 704 and an output device. A user may make use of an input device, such as a computer mouse, stylus, track ball, keyboard, and/or any other similar device capable of receiving user actions and/or motions as input signals. Likewise, a user may make use of an output device, such as a display, a printer, etc., and/or any other device capable of providing signals and/or generating stimuli for a user, such as visual stimuli, audio stimuli and/or other similar stimuli.

In the preceding description, various aspects of claimed subject matter have been described. For purposes of explanation, specifics, such as amounts, systems and/or configurations, as examples, were set forth. In other instances, well-known features were omitted and/or simplified so as not to obscure claimed subject matter. While certain features have been illustrated and/or described herein, many modifications, substitutions, changes and/or equivalents will now occur to those skilled in the art. It is, therefore, to be understood that the appended claims are intended to cover all modifications and/or changes as fall within claimed subject matter.

What is claimed is:

1. An apparatus for tracking behavioral content for a particular user, comprising:
at least one processor to track signals and/or states representative of the behavioral profile content for the particular user, the behavioral profile content to include a plurality of parameters representative of a current behavioral state of the particular user;
at least one memory to store the tracked signals and/or states representative of the behavioral content;
wherein the at least one processor to perform one or more machine learning operations to determine one or more relationships between the tracked signals and/or states representative of the behavioral profile content and bioavailability or balance, or a combination thereof, of one or more particular substances within the particular user's body.

2. The apparatus of claim 1, wherein the signals and/or states representative of the behavioral profile content to further include a plurality of parameters representative of a current biological state of the particular user, wherein the at least one processor further to generate one or more recommendations for supplementation related to the one or more particular substances within the particular user's body, the one or more recommendations to be directed to improvement of a subsequent state of the particular user, wherein the at least one processor to generate the one or more recommendations to be based at least in part on current behavioral profile content for the particular user or to be based at least in part on the one or more determined relationships, or a combination thereof.

3. The apparatus of claim 2, wherein the behavioral profile content to comprise one or more parameters representative of eye movement for the particular user.

4. The apparatus of claim 3, wherein to perform the one or more machine learning operations, the at least one processor to perform one or more training operations to be based at least in part on input to be obtained from one or more users, wherein the input to include content representative of intake by the particular user of supplementation related to the one or more particular substances within the particular user's body.

5. The apparatus of claim 3, wherein the one or more particular substances within the particular user's body to comprise gamma-aminobutyric acid (GABA) or glutamate, or a combination thereof.

6. The apparatus of claim 5, wherein the at least one processor to perform the one or more machine learning operations to determine the one or more relationships between the one or more parameters representative of the eye movement and a balance between the GABA and the glutamate within the particular user's body.

7. The apparatus of claim 3, wherein the one or more particular substances within the particular user's body to comprise 5-methyltetrahydrofolate (5-MTHF).

8. The apparatus of claim 7, wherein the at least one processor to perform the one or more machine learning operations to determine the one or more relationships between the one or more parameters representative of the eye movement and a bioavailability of the 5-MTHF within the particular user's body.

9. The apparatus of claim 2, wherein the behavioral profile content to comprise one or more parameters representative of voice tonality, sentiment analysis, volume, frequency, pitch or timbre, or any combination thereof, for the particular user, and wherein the one or more particular substances within the particular user's body to comprise 5-MTHF.

10. The apparatus of claim 1, wherein the at least one processor further to track signals and/or states representative of environmental noise associated with the particular user, and wherein the at least one processor to perform one or more additional machine learning operations to determine one or more relationships between the tracked environmental noise and a change in balance of one or more hormones including testosterone, estrogen or progesterone, or a combination thereof.

11. A method for tracking behavioral content for a particular user, comprising:
tracking, via at least one processor, signals and/or states representative of the behavioral profile content for the particular user, wherein the behavioral profile content includes a plurality of parameters representative of a current behavioral state of the particular user;
storing the tracked signals and/or states representative of the behavioral content in at least one memory;
determining, at least in part via the at least one processor performing one or more machine learning operations, one or more relationships between the stored and tracked signals and/or states representative of the behavioral profile content and bioavailability or balance, or a combination thereof, of one or more particular substances within the particular user's body.

12. The method of claim 11, wherein the behavioral profile content further includes a plurality of parameters representative of a current biological state of the particular user, and further comprising generating, at least in part via the at least one processor, one or more recommendations for supplementation related to the one or more particular substances within the particular user's body based at least in part on current behavioral profile content for the particular user or based at least in part on the one or more determined relationships, or a combination thereof, wherein the one or more recommendations are directed to improvement of a subsequent state of the particular user.

13. The method of claim 12, wherein the behavioral profile content comprises one or more parameters representative of eye movement for the particular user.

14. The method of claim 13, wherein the performing the one or more machine learning operations comprises performing one or more training operations based at least in part on input obtained from one or more users, wherein the input obtained from one or more users to include content representative of intake by the particular user of supplementation related to the one or more particular substances within the particular user's body.

15. The method of claim 13, wherein the one or more particular substances within the particular user's body comprises gamma-aminobutyric acid (GABA) or glutamate, or a combination thereof.

16. The method of claim 15, wherein the determining the one or more relationships between the tracked behavioral profile content and the bioavailability or balance, or a combination thereof, of the one or more particular substances within the particular user's body comprises determining one or more relationships between the one or more parameters representative of the eye movement and a balance between the GABA and the glutamate within the particular user's body.

17. The method of claim 13, wherein the one or more particular substances within the particular user's body comprises 5-methyltetrahydrofolate.

18. The method of claim 17, wherein the determining the one or more relationships between the tracked signals and/or states representative of the behavioral profile content and the bioavailability or balance, or a combination thereof, of the one or more particular substances within the particular user's body comprises determining one or more relationships between the one or more parameters representative of the eye movement and a bioavailability of the 5-methyltetrahydrofolate within the particular user's body.

19. The method of claim 12, wherein the behavioral profile content comprises one or more parameters representative of voice tonality, sentiment analysis, volume, frequency, pitch or timbre, or any combination thereof, for the particular user, and wherein the one or more particular substances within the particular user's body comprises 5-MTHF.

20. The method of claim 15, wherein the behavioral profile content includes one or more parameters indicative of one or more locations visited by the particular user, and wherein the determining the one or more relationships between the tracked signals and/or states representative of the behavioral profile content and the bioavailability or balance, or the combination thereof, of the one or more particular substances within the particular user's body comprises identifying one or more locations at which a glutamate/GABA balance has been manipulated at least in part by identifying one or more changes in the glutamate/GABA balance and identifying one or more locations at which the changes occurred.

* * * * *